United States Patent
Natsch et al.

(10) Patent No.: US 9,109,246 B2
(45) Date of Patent: Aug. 18, 2015

(54) ENZYMATIC METHODS AND ENZYMES

(75) Inventors: Andreas Natsch, Uetikon (CH); Roger Emter, Munchenstein (CH)

(73) Assignee: Givaudan SA, Vernier (CH)

( * ) Notice: Subject to any disclaimer, the term of this patent is extended or adjusted under 35 U.S.C. 154(b) by 1529 days.

(21) Appl. No.: 12/682,106

(22) PCT Filed: Oct. 8, 2008

(86) PCT No.: PCT/CH2008/000419
§ 371 (c)(1),
(2), (4) Date: Apr. 8, 2010

(87) PCT Pub. No.: WO2009/046557
PCT Pub. Date: Apr. 16, 2009

(65) Prior Publication Data
US 2010/0222429 A1    Sep. 2, 2010

Related U.S. Application Data

(60) Provisional application No. 60/978,815, filed on Oct. 10, 2007.

(51) Int. Cl.
| | |
|---|---|
| *C12N 9/48* | (2006.01) |
| *A61K 31/195* | (2006.01) |
| *C12N 9/99* | (2006.01) |
| *C12P 1/06* | (2006.01) |
| *C07H 21/04* | (2006.01) |
| *C12Q 1/37* | (2006.01) |
| *C12N 9/52* | (2006.01) |

(52) U.S. Cl.
CPC .. *C12Q 1/37* (2013.01); *C12N 9/52* (2013.01); *G01N 2500/02* (2013.01); *G01N 2800/00* (2013.01)

(58) Field of Classification Search
CPC . C12N 9/52; G01N 2500/02; G01N 2800/00; C12Q 1/37
See application file for complete search history.

(56) References Cited

FOREIGN PATENT DOCUMENTS

| | | |
|---|---|---|
| EP | 1108790 A2 | 6/2001 |
| EP | 1258531 A1 | 11/2002 |
| EP | 1852508 A2 | 11/2007 |
| WO | 2006079934 A | 8/2006 |

OTHER PUBLICATIONS

Natsch et al., Enzyme Catalysis and Regulation: A Specific Bacterial Aminoacylase Cleaves Odorant precursors Secreted in the Human Axila, The Journal of Biological Chemistry, (2003) vol. 278, Issues Feb. 21, pp. 5718-5727.*
Wikipedia, Excipient, Accessed Nov. 22, 2014 online at: en.wikipedia.org/wiki/Excipient.*
XP002509176, The Complete Genome Sequence and Analysis of *Corynebacterium diptheriae* NCTC13129, Ceredeno-Tarraga A M, Nucleic Acids Research, vol. 31, No. 22, pp. 6516-6523, Nov. 2003.
XP002509180, SubName: Full=Putative Peptidase, Database UniProt, Jul. 2004.
XP002509177, Complete Genome Sequence and Analysis of the Multiresistant Nosocomial Pathogen *Corynebacterium jeikeium* K411, a Lipid-Requiring Bacterium of the Human Skin Flora, Andreas Tauch, Journal of Bacteriology, vol. 187, No. 13, pp. 4671-7682, Jul. 2005.
XP002509181, SubName: Full=Putative Peptidase, Database UniProt, Aug. 2005.
XP002509178 Isolation of a Bacterial Enzyme Releasing Axillary Malodor and its Use as a Screening Target for Novel Deodorant Formulations, Andreas Natsch, International Journal of Cosmetic Science, vol. 27, No. 2, pp. 115-122, Apr. 2005.
XP002509179, The Sequential Action of a Dipeptidase and a Beta-Lyase is Required for the Release of the Human Body Odorant 3-mthyl-3-sulfanylhexan-1 ol from a Secreted Cys-Gly-(S) Conjugate by *Corynebacteria*, Roger Emter, The Journal of Biological Chemistry, vol. 283, No. 30, pp. 20645-20652, Jul. 2008.
XP002509182, The Sequential Action of a Dipeptidase and a Beta-Lyase is Required for the Release of the Human Body Odorant 3-Methyl-3-Sulfanylhexan-1 ol from a Secreted Cys-Gly-(S) Conjugate by *Corynebacteria*, ROger Emter, The Journal of Biological Chemistry, vol. 283, No. 30, pp. 20645-20652, Jul. 2008.
XP002509183, Sequence 9010 from Patent EP1852508, Database EPO Proteins, Sep. 2008.

* cited by examiner

*Primary Examiner* — Karen Cochrane Carlson
*Assistant Examiner* — Jennifer M. H. Tichy
(74) *Attorney, Agent, or Firm* — Norris McLaughlin & Marcus PA

(57) ABSTRACT

Provided are methods to identify modulators and in particular inhibitors of body malodour formation employing peptidase enzymes, the peptidase enzymes and corresponding nucleotide sequences, expression vectors, transfected host cells, methods of forming the peptidase enzymes and methods to prevent body malodour.

3 Claims, No Drawings

SEQUENCE LISTING

```
<160> NUMBER OF SEQ ID NOS: 6

<210> SEQ ID NO 1
<211> LENGTH: 1368
<212> TYPE: DNA
<213> ORGANISM: Corynebacterium sp. Ax20
<220> FEATURE:
<221> NAME/KEY: CDS
<222> LOCATION: (1)..(1368)

<400> SEQUENCE: 1 atg agc aac gac aag gca gca acc agc acg aat ttc aac ctg acg ccg        48
Met Ser Asn Asp Lys Ala Ala Thr Ser Thr Asn Phe Asn Leu Thr Pro
1               5                   10                  15 aac cgg gag cgc atc ttc cag gag ctc tcg gag cta atc tcc cac tac        96
Asn Arg Glu Arg Ile Phe Gln Glu Leu Ser Glu Leu Ile Ser His Tyr
                20                  25                  30 tcg ccg cac tcg atg ccg gag cac gcc gac acc cac gag gag gcc gcg       144
Ser Pro His Ser Met Pro Glu His Ala Asp Thr His Glu Glu Ala Ala
            35                  40                  45 aag tgg gtg acc gcc aag ctc gag gag ctc ggc ctc gat gtc acc cgc       192
Lys Trp Val Thr Ala Lys Leu Glu Glu Leu Gly Leu Asp Val Thr Arg
        50                  55                  60 cac ccg acg gtg gat gat gcg gac acc atc atc ggc gtg aag gaa cca       240
His Pro Thr Val Asp Asp Ala Asp Thr Ile Ile Gly Val Lys Glu Pro
65                  70                  75                  80 gtg ggc gac gcc ccg acc atc ctc ctc tac tcg cac tac gac gtc gtc       288
Val Gly Asp Ala Pro Thr Ile Leu Leu Tyr Ser His Tyr Asp Val Val
                85                  90                  95 ccc gca cag aac cct gcc gtg tgg acg aac gac ccg ctc gag ctc gat       336
Pro Ala Gln Asn Pro Ala Val Trp Thr Asn Asp Pro Leu Glu Leu Asp
                100                 105                 110 gag cgg gat ggc cgc tgg tac ggc cgc ggg gcc gcg gac tgc aag ggc       384
Glu Arg Asp Gly Arg Trp Tyr Gly Arg Gly Ala Ala Asp Cys Lys Gly
            115                 120                 125 aac gtc atc atg cac ctc gag gcc ctc cgc atg gtc cag gaa aac ggc       432
Asn Val Ile Met His Leu Glu Ala Leu Arg Met Val Gln Glu Asn Gly
        130                 135                 140 ggc acc gac ctc ggc ctc aag gtg gtc atg gaa ggt tcg gaa gag ctc       480
Gly Thr Asp Leu Gly Leu Lys Val Val Met Glu Gly Ser Glu Glu Leu
145                 150                 155                 160 ggc ggc gag gac ggc ctg ggc aag ctc atc gac gcc aac cct gag ctg       528
Gly Gly Glu Asp Gly Leu Gly Lys Leu Ile Asp Ala Asn Pro Glu Leu
                165                 170                 175 ttc acc gca gac gtc att ttc atc ggc gac ggt ggc aac gtg gcc gtc       576
Phe Thr Ala Asp Val Ile Phe Ile Gly Asp Gly Gly Asn Val Ala Val
                180                 185                 190 ggc atc ccg acc ttg acc acc cat ctg cgc ggt ggc gca cag ctg cgc       624
Gly Ile Pro Thr Leu Thr Thr His Leu Arg Gly Gly Ala Gln Leu Arg
            195                 200                 205 ttc aag gtg gat acc ctc gag ggc ccg gtc cac tcc ggt ggt tgg ggc       672
Phe Lys Val Asp Thr Leu Glu Gly Pro Val His Ser Gly Gly Trp Gly
        210                 215                 220 ggc gcg gcc ccg gat gcg gcg cac gca ctg atc cgc atc atc gat tcc       720
Gly Ala Ala Pro Asp Ala Ala His Ala Leu Ile Arg Ile Ile Asp Ser
225                 230                 235                 240
```

```
ttc ttc gac gag cac ggc cgc acc acg atc gag ggc gtg gac act acc      768
Phe Phe Asp Glu His Gly Arg Thr Thr Ile Glu Gly Val Asp Thr Thr
                245                 250                 255 gcg aag tgg gag ggc gat ccg tac gac cgc gag acc ttc cgc aag gac      816
Ala Lys Trp Glu Gly Asp Pro Tyr Asp Arg Glu Thr Phe Arg Lys Asp
            260                 265                 270 gcc cgc gtc ctc gac ggc gtg cag ctg ctg ggc acc gtc gac gac gaa      864
Ala Arg Val Leu Asp Gly Val Gln Leu Leu Gly Thr Val Asp Asp Glu
        275                 280                 285 ccg gcg gac atg gtg tgg gct cgc ccg gca atc acc gtc atc ggg ttc      912
Pro Ala Asp Met Val Trp Ala Arg Pro Ala Ile Thr Val Ile Gly Phe
    290                 295                 300 acc tcg gtg ccg gtg gag gac gcg acc aac atc gtg aac ccg acc gcc      960
Thr Ser Val Pro Val Glu Asp Ala Thr Asn Ile Val Asn Pro Thr Ala
305                 310                 315                 320 gag gca cag ttc aac ctg cgc gtg ccc gca ccg cag tcc gct gct gag     1008
Glu Ala Gln Phe Asn Leu Arg Val Pro Ala Pro Gln Ser Ala Ala Glu
                325                 330                 335 gta gcg aag aag gtc gag gag cag atc cgc gca cgc gcc ccg tgg ggc     1056
Val Ala Lys Lys Val Glu Glu Gln Ile Arg Ala Arg Ala Pro Trp Gly
            340                 345                 350 gca aag gtc gag gtg agc atc acc ggc gtg aac gag ccg ttc tcc acc     1104
Ala Lys Val Glu Val Ser Ile Thr Gly Val Asn Glu Pro Phe Ser Thr
        355                 360                 365 gac ccg aac ggc ccg gcg gtg cag cac ttc ggc aag tgc ctg cag gac     1152
Asp Pro Asn Gly Pro Ala Val Gln His Phe Gly Lys Cys Leu Gln Asp
    370                 375                 380 gcc tac ggc gcg gag cac ctc acc gtg gtc ggc acc ggt ggc tcc atc     1200
Ala Tyr Gly Ala Glu His Leu Thr Val Val Gly Thr Gly Gly Ser Ile
385                 390                 395                 400 ccg ctg act gtg acc ctg cag aag cac ttc ccg gac gca gag ttc gcg     1248
Pro Leu Thr Val Thr Leu Gln Lys His Phe Pro Asp Ala Glu Phe Ala
                405                 410                 415 ctc tac ggc gtc gcg gat ccg gcc gcg aac atc cac ggc gtc gac gag     1296
Leu Tyr Gly Val Ala Asp Pro Ala Ala Asn Ile His Gly Val Asp Glu
            420                 425                 430 tcc gtc gat ccg acg gag atc gag cac gtc gct att gcc gaa gca gaa     1344
Ser Val Asp Pro Thr Glu Ile Glu His Val Ala Ile Ala Glu Ala Glu
        435                 440                 445 ttc ctg ctc acc tac ggg aaa tag                                      1368
Phe Leu Leu Thr Tyr Gly Lys
    450                 455

<210> SEQ ID NO 2
<211> LENGTH: 455
<212> TYPE: PRT
<213> ORGANISM: Corynebacterium sp. Ax20

<400> SEQUENCE: 2

Met Ser Asn Asp Lys Ala Ala Thr Ser Thr Asn Phe Asn Leu Thr Pro
1               5                   10                  15

Asn Arg Glu Arg Ile Phe Gln Glu Leu Ser Glu Leu Ile Ser His Tyr
            20                  25                  30

Ser Pro His Ser Met Pro Glu His Ala Asp Thr His Glu Glu Ala Ala
        35                  40                  45

Lys Trp Val Thr Ala Lys Leu Glu Glu Leu Gly Leu Asp Val Thr Arg
    50                  55                  60

His Pro Thr Val Asp Asp Ala Asp Thr Ile Ile Gly Val Lys Glu Pro
65                  70                  75                  80
```

```
Val Gly Asp Ala Pro Thr Ile Leu Leu Tyr Ser His Tyr Asp Val Val
                85                  90                  95

Pro Ala Gln Asn Pro Ala Val Trp Thr Asn Asp Pro Leu Glu Leu Asp
            100                 105                 110

Glu Arg Asp Gly Arg Trp Tyr Gly Arg Gly Ala Ala Asp Cys Lys Gly
        115                 120                 125

Asn Val Ile Met His Leu Glu Ala Leu Arg Met Val Gln Glu Asn Gly
    130                 135                 140

Gly Thr Asp Leu Gly Leu Lys Val Val Met Glu Gly Ser Glu Glu Leu
145                 150                 155                 160

Gly Gly Glu Asp Gly Leu Gly Lys Leu Ile Asp Ala Asn Pro Glu Leu
                165                 170                 175

Phe Thr Ala Asp Val Ile Phe Ile Gly Asp Gly Gly Asn Val Ala Val
            180                 185                 190

Gly Ile Pro Thr Leu Thr Thr His Leu Arg Gly Gly Ala Gln Leu Arg
        195                 200                 205

Phe Lys Val Asp Thr Leu Glu Gly Pro Val His Ser Gly Gly Trp Gly
    210                 215                 220

Gly Ala Ala Pro Asp Ala Ala His Ala Leu Ile Arg Ile Ile Asp Ser
225                 230                 235                 240

Phe Phe Asp Glu His Gly Arg Thr Thr Ile Glu Gly Val Asp Thr Thr
                245                 250                 255

Ala Lys Trp Glu Gly Asp Pro Tyr Asp Arg Glu Thr Phe Arg Lys Asp
            260                 265                 270

Ala Arg Val Leu Asp Gly Val Gln Leu Leu Gly Thr Val Asp Asp Glu
        275                 280                 285

Pro Ala Asp Met Val Trp Ala Arg Pro Ala Ile Thr Val Ile Gly Phe
    290                 295                 300

Thr Ser Val Pro Val Glu Asp Ala Thr Asn Ile Val Asn Pro Thr Ala
305                 310                 315                 320

Glu Ala Gln Phe Asn Leu Arg Val Pro Ala Pro Gln Ser Ala Ala Glu
                325                 330                 335

Val Ala Lys Lys Val Glu Gln Ile Arg Ala Arg Ala Pro Trp Gly
            340                 345                 350

Ala Lys Val Glu Val Ser Ile Thr Gly Val Asn Glu Pro Phe Ser Thr
        355                 360                 365

Asp Pro Asn Gly Pro Ala Val Gln His Phe Gly Lys Cys Leu Gln Asp
    370                 375                 380

Ala Tyr Gly Ala Glu His Leu Thr Val Val Gly Thr Gly Gly Ser Ile
385                 390                 395                 400

Pro Leu Thr Val Thr Leu Gln Lys His Phe Pro Asp Ala Glu Phe Ala
                405                 410                 415

Leu Tyr Gly Val Ala Asp Pro Ala Ala Asn Ile His Gly Val Asp Glu
            420                 425                 430

Ser Val Asp Pro Thr Glu Ile Glu His Val Ala Ile Ala Glu Ala Glu
        435                 440                 445

Phe Leu Leu Thr Tyr Gly Lys
    450                 455

<210> SEQ ID NO 3
<211> LENGTH: 1404
<212> TYPE: DNA
<213> ORGANISM: Corynebacterium jeikeium K411
<220> FEATURE:
```

<220> NAME/KEY: CDS
<222> LOCATION: (1)..(1404)

<400> SEQUENCE: 3

```
atg agc gat acc aac agt gaa tcc aac acc tca cag cta gac cta gcc      48
Met Ser Asp Thr Asn Ser Glu Ser Asn Thr Ser Gln Leu Asp Leu Ala
1               5                   10                  15 cgc gcc gcc atc gcg gag cag atg cca caa ctg aag gaa gac ctc acc      96
Arg Ala Ala Ile Ala Glu Gln Met Pro Gln Leu Lys Glu Asp Leu Thr
                20                  25                  30 acc ctg gtc tcc ttc gag tcg gtc cac tct gcc cca ggc ctg gaa gag     144
Thr Leu Val Ser Phe Glu Ser Val His Ser Ala Pro Gly Leu Glu Glu
            35                  40                  45 gcc aat gct gct gcc gca caa tgg gtc atc gac aca ttc acc agc gtg     192
Ala Asn Ala Ala Ala Ala Gln Trp Val Ile Asp Thr Phe Thr Ser Val
        50                  55                  60 ggc atc ccc gtc gaa ggt cac gtc acc acc gac ggc tcc acc tcc gtc     240
Gly Ile Pro Val Glu Gly His Val Thr Thr Asp Gly Ser Thr Ser Val
65                  70                  75                  80 atc ggc cta cgc gag ccc gct gag ggc tac cca acc atc ctc cta tac     288
Ile Gly Leu Arg Glu Pro Ala Glu Gly Tyr Pro Thr Ile Leu Leu Tyr
                85                  90                  95 tcc cac ttc gac gtg cag ccc gcc ggc gac atc gag gcg tgg acc aat     336
Ser His Phe Asp Val Gln Pro Ala Gly Asp Ile Glu Ala Trp Thr Asn
                100                 105                 110 gac ccc tgg acc ctt acc gaa cgc gat ggc cgc tgg tac ggc cgc ggt     384
Asp Pro Trp Thr Leu Thr Glu Arg Asp Gly Arg Trp Tyr Gly Arg Gly
            115                 120                 125 acc gcc gac tgc aag ggt cac gtc gcc atg cac gtt gct gtg ctg cgt     432
Thr Ala Asp Cys Lys Gly His Val Ala Met His Val Ala Val Leu Arg
        130                 135                 140 gct ctt tct att ctt tcg gac gcc cac ttc ccc gcc gcc aag aat ctc     480
Ala Leu Ser Ile Leu Ser Asp Ala His Phe Pro Ala Ala Lys Asn Leu
145                 150                 155                 160 ggc atc cgg atc gtc gtc gag ggc tcg gag gaa cgc ggc gga tat ggc     528
Gly Ile Arg Ile Val Val Glu Gly Ser Glu Glu Arg Gly Gly Tyr Gly
                165                 170                 175 ctg gag gac ctg cta gcc gaa aag ccg gag ctc ttc gcg gcc gat acc     576
Leu Glu Asp Leu Leu Ala Glu Lys Pro Glu Leu Phe Ala Ala Asp Thr
                180                 185                 190 ttc ctt att gcc gac tcc ggc aat gac gcc ctg ggt gag ccg agc ctg     624
Phe Leu Ile Ala Asp Ser Gly Asn Asp Ala Leu Gly Glu Pro Ser Leu
            195                 200                 205 tgc acc gcg ctg cgc ggc tcc gcg ccg gtc acg gtg cgc acc cgc acg     672
Cys Thr Ala Leu Arg Gly Ser Ala Pro Val Thr Val Arg Thr Arg Thr
        210                 215                 220 ctg gcg cag ccg atg cac tcc ggc cag ttc ggt ggc tcg gca ccg gat     720
Leu Ala Gln Pro Met His Ser Gly Gln Phe Gly Gly Ser Ala Pro Asp
225                 230                 235                 240 gcc ctg gtt gag ctg gtg caa ctc ctt tcc act ctc cat gac gaa aac     768
Ala Leu Val Glu Leu Val Gln Leu Leu Ser Thr Leu His Asp Glu Asn
                245                 250                 255 ggc cta gtg gcc gtc ccg gga ttg gag ccc aag gag cgc tgg ggt ggc     816
Gly Leu Val Ala Val Pro Gly Leu Glu Pro Lys Glu Arg Trp Gly Gly
                260                 265                 270 gtc gga cca aca gaa cag gaa ttc cgc gac aac gcc gga gta acc gac     864
Val Gly Pro Thr Glu Gln Glu Phe Arg Asp Asn Ala Gly Val Thr Asp
            275                 280                 285 ggc gtg gag cta tac gga gcc ggc gaa tgg cag ccg aac gac ctg acg     912
Gly Val Glu Leu Tyr Gly Ala Gly Glu Trp Gln Pro Asn Asp Leu Thr
```

```
                  290                 295                 300
gtg atg aac cca tcg att acg atc aca ggc ctg gat gca ctg tcg gtg    960
Val Met Asn Pro Ser Ile Thr Ile Thr Gly Leu Asp Ala Leu Ser Val
305                 310                 315                 320 gcg gac tcg gtg aac tcc gtg ccg gcg acc gca gcg gcc gtg gtg agc   1008
Ala Asp Ser Val Asn Ser Val Pro Ala Thr Ala Ala Ala Val Val Ser
                325                 330                 335 ctg cgc gtg ccg ccg gga cgc gag ccg cag gag tgc cag gat ctg ctg   1056
Leu Arg Val Pro Pro Gly Arg Glu Pro Gln Glu Cys Gln Asp Leu Leu
            340                 345                 350 gtc aag cac ttg gaa agc cag aag aca aac gca cta gtg gag atc gaa   1104
Val Lys His Leu Glu Ser Gln Lys Thr Asn Ala Leu Val Glu Ile Glu
        355                 360                 365 cgc ggc tcc ttg gca gag gca ttc cag gcg gat acc tcc ggc ccg gca   1152
Arg Gly Ser Leu Ala Glu Ala Phe Gln Ala Asp Thr Ser Gly Pro Ala
370                 375                 380 ctg cag cgg ctc ggc gag gcg ctg ggc gag gtg tac ggc aag gag acg   1200
Leu Gln Arg Leu Gly Glu Ala Leu Gly Glu Val Tyr Gly Lys Glu Thr
385                 390                 395                 400 atg gag gtc gcc tcc ggc ggg tca atc cca cta acg aac aag ctg ctg   1248
Met Glu Val Ala Ser Gly Gly Ser Ile Pro Leu Thr Asn Lys Leu Leu
                405                 410                 415 ggt gcg tac ccg cag gcg gag ctc gcg cta tac ggc atc gag gag ccg   1296
Gly Ala Tyr Pro Gln Ala Glu Leu Ala Leu Tyr Gly Ile Glu Glu Pro
            420                 425                 430 aag tgc gcc atc cac tcc gcg gac gaa tcc gtg gat ccg ggt gag atc   1344
Lys Cys Ala Ile His Ser Ala Asp Glu Ser Val Asp Pro Gly Glu Ile
        435                 440                 445 gag gcc atc gcg acg gca gag cta ctg ttc ctg cta cgc acc gcc gag   1392
Glu Ala Ile Ala Thr Ala Glu Leu Leu Phe Leu Leu Arg Thr Ala Glu
450                 455                 460 gcg cac agc tag                                                   1404
Ala His Ser
465

<210> SEQ ID NO 4
<211> LENGTH: 467
<212> TYPE: PRT
<213> ORGANISM: Corynebacterium jeikeium K411

<400> SEQUENCE: 4

Met Ser Asp Thr Asn Ser Glu Ser Asn Thr Ser Gln Leu Asp Leu Ala
1               5                   10                  15

Arg Ala Ala Ile Ala Glu Gln Met Pro Gln Leu Lys Glu Asp Leu Thr
            20                  25                  30

Thr Leu Val Ser Phe Glu Ser Val His Ser Ala Pro Gly Leu Glu Glu
        35                  40                  45

Ala Asn Ala Ala Ala Ala Gln Trp Val Ile Asp Thr Phe Thr Ser Val
    50                  55                  60

Gly Ile Pro Val Glu Gly His Val Thr Thr Asp Gly Thr Ser Val
65                  70                  75                  80

Ile Gly Leu Arg Glu Pro Ala Glu Gly Tyr Pro Thr Ile Leu Leu Tyr
                85                  90                  95

Ser His Phe Asp Val Gln Pro Ala Gly Asp Ile Glu Ala Trp Thr Asn
            100                 105                 110

Asp Pro Trp Thr Leu Thr Glu Arg Asp Gly Arg Trp Tyr Gly Arg Gly
        115                 120                 125

Thr Ala Asp Cys Lys Gly His Val Ala Met His Val Ala Val Leu Arg
```

```
                    130                 135                 140
Ala Leu Ser Ile Leu Ser Asp Ala His Phe Pro Ala Ala Lys Asn Leu
145                 150                 155                 160

Gly Ile Arg Ile Val Val Glu Gly Ser Glu Arg Gly Gly Tyr Gly
                165                 170                 175

Leu Glu Asp Leu Leu Ala Glu Lys Pro Glu Leu Phe Ala Ala Asp Thr
                180                 185                 190

Phe Leu Ile Ala Asp Ser Gly Asn Asp Ala Leu Gly Glu Pro Ser Leu
            195                 200                 205

Cys Thr Ala Leu Arg Gly Ser Ala Pro Val Thr Val Arg Thr Arg Thr
        210                 215                 220

Leu Ala Gln Pro Met His Ser Gly Gln Phe Gly Ser Ala Pro Asp
225                 230                 235                 240

Ala Leu Val Glu Leu Val Gln Leu Leu Ser Thr Leu His Asp Glu Asn
                245                 250                 255

Gly Leu Val Ala Val Pro Gly Leu Glu Pro Lys Glu Arg Trp Gly Gly
                260                 265                 270

Val Gly Pro Thr Glu Gln Glu Phe Arg Asp Asn Ala Gly Val Thr Asp
            275                 280                 285

Gly Val Glu Leu Tyr Gly Ala Gly Glu Trp Gln Pro Asn Asp Leu Thr
290                 295                 300

Val Met Asn Pro Ser Ile Thr Ile Thr Gly Leu Asp Ala Leu Ser Val
305                 310                 315                 320

Ala Asp Ser Val Asn Ser Val Pro Ala Thr Ala Ala Val Val Ser
                325                 330                 335

Leu Arg Val Pro Pro Gly Arg Glu Pro Gln Glu Cys Gln Asp Leu Leu
                340                 345                 350

Val Lys His Leu Glu Ser Gln Lys Thr Asn Ala Leu Val Glu Ile Glu
                355                 360                 365

Arg Gly Ser Leu Ala Glu Ala Phe Gln Ala Asp Thr Ser Gly Pro Ala
        370                 375                 380

Leu Gln Arg Leu Gly Glu Ala Leu Gly Glu Val Tyr Gly Lys Glu Thr
385                 390                 395                 400

Met Glu Val Ala Ser Gly Ser Ile Pro Leu Thr Asn Lys Leu Leu
                405                 410                 415

Gly Ala Tyr Pro Gln Ala Glu Leu Ala Leu Tyr Gly Ile Glu Glu Pro
            420                 425                 430

Lys Cys Ala Ile His Ser Ala Asp Glu Ser Val Asp Pro Gly Glu Ile
        435                 440                 445

Glu Ala Ile Ala Thr Ala Glu Leu Leu Phe Leu Leu Arg Thr Ala Glu
    450                 455                 460

Ala His Ser
465

<210> SEQ ID NO 5
<211> LENGTH: 1134
<212> TYPE: DNA
<213> ORGANISM: Corynebacterium sp. Ax 20
<220> FEATURE:
<221> NAME/KEY: CDS
<222> LOCATION: (1)..(1134)

<400> SEQUENCE: 5 atg cag ttc tcc aac ctt gac acc ctg cgc acc cgt ggc acc cgc aag    48
Met Gln Phe Ser Asn Leu Asp Thr Leu Arg Thr Arg Gly Thr Arg Lys
1               5                  10                  15
```

-continued

| | |
|---|---|
| tgg acc cag ttc gac gac gac gtc atc ccc atg ttc gtc gcc gag agc<br>Trp Thr Gln Phe Asp Asp Asp Val Ile Pro Met Phe Val Ala Glu Ser<br>20                          25                 30 | 96 |
| gac ttc ccc acc gca cca gcc atc aag gaa gcg att atc gac gcc tgc<br>Asp Phe Pro Thr Ala Pro Ala Ile Lys Glu Ala Ile Ile Asp Ala Cys<br>      35                   40                 45 | 144 |
| gag cgc gag atg ttc ggc tac act ccc gcc ccg cac gcg cac cac ctg<br>Glu Arg Glu Met Phe Gly Tyr Thr Pro Ala Pro His Ala His His Leu<br>50                         55                 60 | 192 |
| ggc gaa gcc gtc gct gac ttc tac gac tgg cgc tac ggc tgg cgc ccg<br>Gly Glu Ala Val Ala Asp Phe Tyr Asp Trp Arg Tyr Gly Trp Arg Pro<br>65                    70                 75                80 | 240 |
| gac gcg gcg aag atc ttc ccc gtc gcc gac gtc gtg cgc ggc gtg ctg<br>Asp Ala Ala Lys Ile Phe Pro Val Ala Asp Val Val Arg Gly Val Leu<br>                   85                 90                95 | 288 |
| ctg gca att cag tac ttc act gac ggc gat gtg atc gtc ccg gtg ccg<br>Leu Ala Ile Gln Tyr Phe Thr Asp Gly Asp Val Ile Val Pro Val Pro<br>                 100               105              110 | 336 |
| gcg tac ttc ccg ttc ctg ccg atc gcg gaa gcc gcc ggc cgc aac cgc<br>Ala Tyr Phe Pro Phe Leu Pro Ile Ala Glu Ala Ala Gly Arg Asn Arg<br>         115                 120               125 | 384 |
| atc gac atc agc tcc gac aag ggg ctc gag ggc ggc ctg gac atg gcc<br>Ile Asp Ile Ser Ser Asp Lys Gly Leu Glu Gly Gly Leu Asp Met Ala<br>130                       135               140 | 432 |
| gag gtc gag gag gcg ttc aag aac ggc gcg ggc agc atc atc gtc acc<br>Glu Val Glu Glu Ala Phe Lys Asn Gly Ala Gly Ser Ile Ile Val Thr<br>145                      150               155               160 | 480 |
| aac ccg ttc aac ccg ggc ggc tgg atg ttc aca tcg gaa gag ctc gac<br>Asn Pro Phe Asn Pro Gly Gly Trp Met Phe Thr Ser Glu Glu Leu Asp<br>                 165               170              175 | 528 |
| caa atc tgc gac atc gct cgc cgg tac aag ggc aga gtg ctt gtc gac<br>Gln Ile Cys Asp Ile Ala Arg Arg Tyr Lys Gly Arg Val Leu Val Asp<br>         180                 185               190 | 576 |
| gaa atc cat gca ccg ctc acc tac ggc aaa cgc cac gtc tgc gct gcc<br>Glu Ile His Ala Pro Leu Thr Tyr Gly Lys Arg His Val Cys Ala Ala<br>195                       200               205 | 624 |
| gcg aat aac ccg gat gtt tgc atc acc gtg acg gcg acc tcg aag gcg<br>Ala Asn Asn Pro Asp Val Cys Ile Thr Val Thr Ala Thr Ser Lys Ala<br>210                       215               220 | 672 |
| tgg aat gtc gcg ggg ctg aag tgc gcg cag atg atc ttc acc aac gac<br>Trp Asn Val Ala Gly Leu Lys Cys Ala Gln Met Ile Phe Thr Asn Asp<br>225                      230               235               240 | 720 |
| gag gac gtg aag acc tgg aac gcg atc aac ccg gtg gcc aag gac ggt<br>Glu Asp Val Lys Thr Trp Asn Ala Ile Asn Pro Val Ala Lys Asp Gly<br>                 245               250              255 | 768 |
| gtc ggc acg ctg ggc atc atc gct gcg gaa gcg gcg tac gag tcc ggc<br>Val Gly Thr Leu Gly Ile Ile Ala Ala Glu Ala Ala Tyr Glu Ser Gly<br>         260                 265               270 | 816 |
| cgc gag cac ctc gat tgg cag gtc gag cag ctc aag gct aac cgc gac<br>Arg Glu His Leu Asp Trp Gln Val Glu Gln Leu Lys Ala Asn Arg Asp<br>275                       280               285 | 864 |
| tgg ctc gtg gaa aac ctc ccc agc ctg att ccg ggg atc cgc ttc gaa<br>Trp Leu Val Glu Asn Leu Pro Ser Leu Ile Pro Gly Ile Arg Phe Glu<br>290                       295               300 | 912 |
| atc ccg gat gcc acc tac ctc atg ttc ttg gac ttc aag gac acg aaa<br>Ile Pro Asp Ala Thr Tyr Leu Met Phe Leu Asp Phe Lys Asp Thr Lys<br>305                       310               315               320 | 960 |
| ttg ggc gtc gat aag cct gct gct tac ctg ttg aaa cat gca cga gtg<br>Leu Gly Val Asp Lys Pro Ala Ala Tyr Leu Leu Lys His Ala Arg Val | 1008 |

```
                    325                 330                 335
gcg ctg agt gag ggg gtt gat ttc ggg cct ggt ggc gag cac cgt gcg    1056
Ala Leu Ser Glu Gly Val Asp Phe Gly Pro Gly Gly Glu His Arg Ala
        340                 345                 350 cgg atg aac ttt gcc acc tcg ccg gag atc ctg aag gag gcc acg gag    1104
Arg Met Asn Phe Ala Thr Ser Pro Glu Ile Leu Lys Glu Ala Thr Glu
            355                 360                 365 cgc atc gcc cgc gcg atc gaa gta gtc taa                            1134
Arg Ile Ala Arg Ala Ile Glu Val Val
        370                 375

<210> SEQ ID NO 6
<211> LENGTH: 377
<212> TYPE: PRT
<213> ORGANISM: Corynebacterium sp. Ax 20

<400> SEQUENCE: 6

Met Gln Phe Ser Asn Leu Asp Thr Leu Arg Thr Arg Gly Thr Arg Lys
1               5                   10                  15

Trp Thr Gln Phe Asp Asp Asp Val Ile Pro Met Phe Val Ala Glu Ser
            20                  25                  30

Asp Phe Pro Thr Ala Pro Ala Ile Lys Glu Ala Ile Ile Asp Ala Cys
        35                  40                  45

Glu Arg Glu Met Phe Gly Tyr Thr Pro Ala Pro His Ala His His Leu
    50                  55                  60

Gly Glu Ala Val Ala Asp Phe Tyr Asp Trp Arg Tyr Gly Trp Arg Pro
65                  70                  75                  80

Asp Ala Ala Lys Ile Phe Pro Val Ala Asp Val Val Arg Gly Val Leu
                85                  90                  95

Leu Ala Ile Gln Tyr Phe Thr Asp Gly Asp Val Ile Val Pro Val Pro
            100                 105                 110

Ala Tyr Phe Pro Phe Leu Pro Ile Ala Glu Ala Ala Gly Arg Asn Arg
        115                 120                 125

Ile Asp Ile Ser Ser Asp Lys Gly Leu Glu Gly Gly Leu Asp Met Ala
    130                 135                 140

Glu Val Glu Glu Ala Phe Lys Asn Gly Ala Gly Ser Ile Ile Val Thr
145                 150                 155                 160

Asn Pro Phe Asn Pro Gly Gly Trp Met Phe Thr Ser Glu Glu Leu Asp
                165                 170                 175

Gln Ile Cys Asp Ile Ala Arg Arg Tyr Lys Gly Arg Val Leu Val Asp
            180                 185                 190

Glu Ile His Ala Pro Leu Thr Tyr Gly Lys Arg His Val Cys Ala Ala
        195                 200                 205

Ala Asn Asn Pro Asp Val Cys Ile Thr Val Thr Ala Thr Ser Lys Ala
    210                 215                 220

Trp Asn Val Ala Gly Leu Lys Cys Ala Gln Met Ile Phe Thr Asn Asp
225                 230                 235                 240

Glu Asp Val Lys Thr Trp Asn Ala Ile Asn Pro Val Ala Lys Asp Gly
                245                 250                 255

Val Gly Thr Leu Gly Ile Ile Ala Ala Glu Ala Ala Tyr Glu Ser Gly
            260                 265                 270

Arg Glu His Leu Asp Trp Gln Val Glu Gln Leu Lys Ala Asn Arg Asp
        275                 280                 285

Trp Leu Val Glu Asn Leu Pro Ser Leu Ile Pro Gly Ile Arg Phe Glu
    290                 295                 300
```

-continued

```
Ile Pro Asp Ala Thr Tyr Leu Met Phe Leu Asp Phe Lys Asp Thr Lys
305                 310                 315                 320

Leu Gly Val Asp Lys Pro Ala Ala Tyr Leu Leu Lys His Ala Arg Val
                325                 330                 335

Ala Leu Ser Glu Gly Val Asp Phe Gly Pro Gly Gly Glu His Arg Ala
                340                 345                 350

Arg Met Asn Phe Ala Thr Ser Pro Glu Ile Leu Lys Glu Ala Thr Glu
            355                 360                 365

Arg Ile Ala Arg Ala Ile Glu Val Val
        370                 375
```

ENZYMATIC METHODS AND ENZYMES

This is an application filed under 35 USC 371 of PCT/CH2008/000419, which in turn is based on U.S. Ser. No. 60/978815 filed 10, Oct. 2007.

TECHNICAL FIELD

Provided are methods to identify modulators of body malodour formation employing nucleotides encoding peptidases, constructs for peptidase expression and cells containing such constructs, and the resulting peptidases.

The nucleotides code for proteins which are peptidase enzymes. The peptidases are involved in malodour formation and can be employed in methods to identify modulators, in particular inhibitors, of body malodour formation. These inhibitors have the ability to prevent or reduce malodour formation on the body, in particular the human body.

BACKGROUND

Since the 1950s it is known that sweat secreted by the apocrine glands is odourless and the undesirable smell of sweat only develops through bacterial action. Accordingly, it was concluded that sweat contains malodour precursors and malodourants are released through the enzymatic action of bacteria on said precursors.

Body malodour, including in particular axilla malodour, is due to three main classes of compounds: Sulfanylalcohols, unsaturated or hydroxylated acids, and steroids. The methods described herein are useful to identify inhibitors that prevent the formation of sulfanylalcohols.

Applicant previously identified the malodour precursor for the unsaturated or hydroxylated acids, and the aminoacylase enzyme ("AMRE") forming them (EP 1258531). The AMRE enzyme can be used to screen for inhibitors of the malodour forming enzymes and thereby to identify compounds to prevent or reduce body malodour.

For the release of sulfanylalcohols, applicant identified a cystathionine-β-lyase from *Corynebacterium* sp. Ax20 and a precursor compound (A. Natsch et al., Chemistry & Biodiversity 2004, 1058).

Starkenmann et al. postulated a different β-lyase from *Staphylococcus haemolyticus* releasing sulfanylalcohols from a different precursor, namely the precursor of formula FIII (WO2006079934).

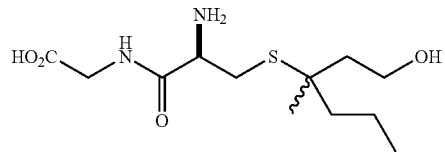

While *Staphylococcus* bacteriae are generally not believed to be involved in malodour formation to a major extent, the compound of FIII (in the examples: "cys-gly-conjugate") seems to contribute to body malodour nonetheless.

The sequence SEQ ID NO: 3, and SEQ ID NO:4 as its hypothetical gene product, were previously published in a sequence database, but the protein function, catalytic activity and its involvement in malodour generation were not known.

Applicant has now surprisingly identified a third type of enzyme (peptidases including but not limited to SEQ ID NO:2 and SEQ ID NO:4) that releases a precursor II from a precursor I (for example, without limitation, compound of FIII) or alternatively, various other substrates described herein below, and together with the action of the previously identified cystationin-β-lyase finally forms a sulfanyl alcohol malodourant (compare FIG. 1).

Both the novel type of peptidase and the β-lyase previously described by applicants occur in *Corynebacteria*. Without wishing to be bound by theory, it is generally accepted that highly unpleasant malodour is released from fresh sweat mainly by *Corynebacteria*.

Applicant showed that no single fraction of *C*. sp. Ax20 extract was able to release malodourant from the precursor I, in particular, without limitation, compound FIII. This demonstrates that there is no single enzyme present in *C*. sp. extracts that can cleave precursor I (compare examples herein-below, in particular example 11). Further applicant showed that two enzymes are mediating the cleavage of precursor I, in particular, without limitation, compound of FIII: first a peptidase (for example, without limitation, SEQ ID NO: 2 or NO:4) cleaving the dipeptide between the gly and the cys residue, and then a β-Lyase subsequently releasing the malodourant from the cys-conjugate (FIV) formed by the peptidase (compare examples herein-below, in particular example 12).

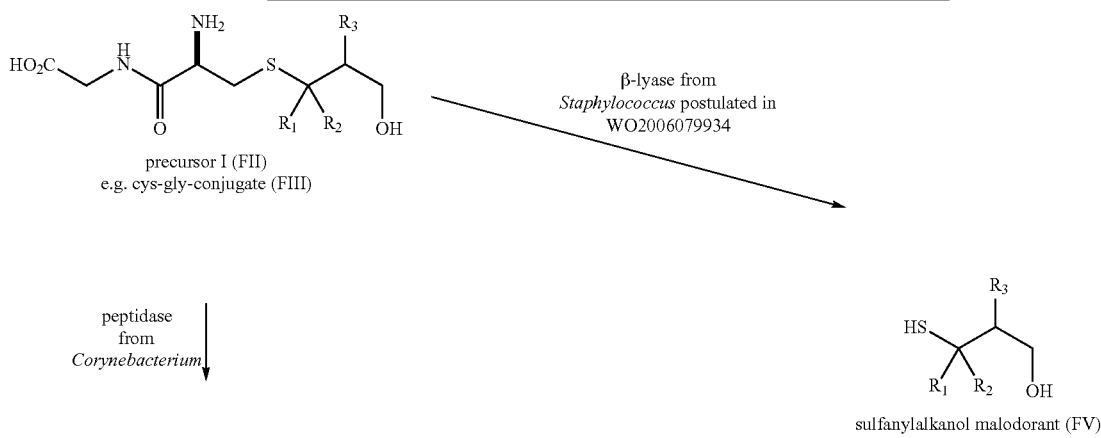

FIG. 1 Reactions of precursors I and II to a sulfanylalkanol malodourant; the reaction from precursor I to precursor II is perfomed by the newly identified peptidase.

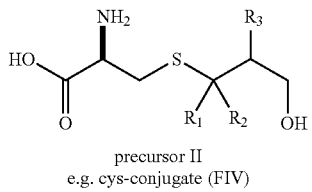

precursor II
e.g. cys-conjugate (FIV)

→ cystathionine-β-lyase from *Corynebacterium* described by Natsch et al. 2004

The identified type of enzyme is useful as an alternative screening target to identify inhibitors of malodour formation by sulfanyl alcohol malodourants.

Precursor I (physiologically relevant substrates) has the general formula FII

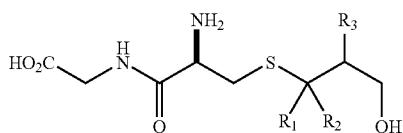

FII wherein R1 is selected from a group of alkane residues consisting of methyl, ethyl, propyl, butyl, pentyl, and hexyl
and wherein R2 and R3 are independently selected from the group consisting of H and methyl.

Accordingly, the sulfanylalkanol malodourant has the general formula FV

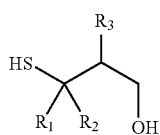

FV wherein R1 is selected from a group of alkane residues consisting of methyl, ethyl, propyl, butyl, pentyl, and hexyl
and wherein R2 and R3 are independently selected from the group consisting of H and methyl.

The peptidases will also react non-physiological substrates of formula FI as detailed herein-below under the section "substrates of peptidase", that are useful for screening purposes.

The type of peptidase enzyme is particularly interesting since, without wishing to be bound by theory, not only does it occur in the most relevant genus of bacteria, but this type of peptidase enzymes seem to perform the rate limiting step in the malodour forming enzymatic reactions, and the identified inhibitors can therefore expected to be particularly effective.

Still further, again without wishing to be bound by theory, both embodiments of peptidase (SEQ ID NO: 2 and SEQ ID NO: 4) belong to the same class of enzymes (metallopeptidases) as the previously identified AMRE enzyme that forms malodourous unsaturated or hydroxylated acids, and screening with the peptidase enzymes (including, without limitation, enzymes of SEQ ID 2 and SEQ ID 4) may result in finding inhibitors also active against the metallopeptidases involved in the formation of malodourous unsaturated or hydroxylated acids and therefore effective to reduce formation of malodourants of both classes at the same time.

SUMMARY

Provided is the following:
(1) A method to identify a modulator of body malodour formation, the method comprising the steps of:
(i) contacting a peptidase with a peptidase substrate and at least one test agent; and
(ii) determining the effect of the at least one test agent on the peptidase-mediated reaction rate,
wherein the peptidase has the catalytic activity to release glycine from the substrate compound of formula FIII

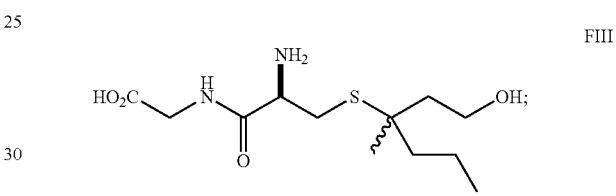

FIII wherein the peptidase is homologous to a polypeptide sequence selected from the group consisting of SEQ ID NO:2 and SEQ ID NO:4 with a sequence identity of at least 40%;
wherein the peptidase comprises the following conserved partial sequences:
ERDGRWYGRGXADCKG between aminoacid 105 and 150,
EGSEEXG between aminoacid 150 and 180,
HSGXXGGXAPDA between aminoacid 205 and 255,
GGSIPL between aminoacid 385 and 425;
and wherein the aminoacids are numbered starting from the N-terminus of the substantially homologous peptidase in its naturally occurring form, and the letters refer to the single character aminoacid code and X is any one of the 20 common aminoacids.

(2) The method of item (1) wherein the peptidase substrate in step (i) is a compound of formula FI

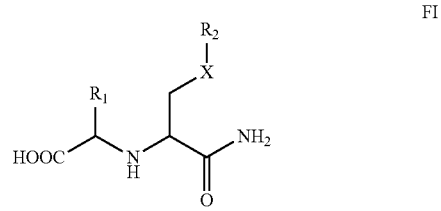

FI wherein X is selected from the group consisting of S and O, and wherein R1 is residue selected from H and methyl, and wherein R2 is a residue selected from the group consisting of a straight or branched C1 to C10 alkyl, a straight or branched C1 to C10 alkanol, a phenyl, and a benzyl.

In an alternative embodiment of item (2), X is S.

(3) The method of item (1) wherein the substrate is a compound selected from the group consisting of S-benzyl-Cys-Gly, O-benzyl-Ser-Gly, (1-(2-hydroxyethyl)-1-methylbutyl)-L-cysteinyl-glycine, S-benzyl-Cys-Ala, O-benzyl-Ser-Ala, Pro-Gly, Ala-Gly, Ala-Ala, and Pro-Ala In an alternative embodiment of item (3), the substrate is a compound selected from the group consisting of S-benzyl-Cys-Gly, O-benzyl-Ser-Gly, (1-(2-hydroxyethyl)-1-methylbutyl)-L-cysteinyl-glycine, S-benzyl-Cys-Ala, and O-benzyl-Ser-Ala.

In an alternative embodiment of item (3), the substrate is a compound selected from the group consisting of Pro-Gly, Ala-Gly, Ala-Ala, Pro-Ala.

(4) The method of any one of items (1) to (3) wherein an additional enzyme, a cystathionine-β-lyase, is incubated with the substrate and the test agent in parallel or subsequently, and wherein in step (ii), the effect of the test agent on cleavage by the peptidase and β-lyase enzymes is determined by the change in formation of at least one of their reaction products, optionally a reaction product selected from a thiol reaction product and a hydroxy reaction product.

(5) A kit comprising:
(i) a peptidase as described herein, in particular as defined under item (1), and
(ii) a substrate compound that is cleaved by the peptidase, for combined use to identify test agents as modulators of the peptidase and malodour formation.

In one particular embodiment of item (5), the substrate compound is a compound of formula FI

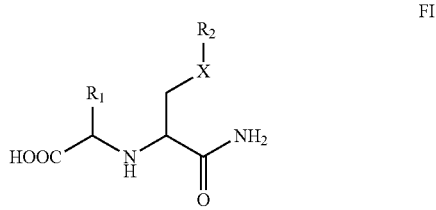

FI wherein X is selected from the group consisting of S and O, and wherein R1 is residue selected from H and methyl, and wherein R2 is a residue selected from the group consisting of a straight or branched C1 to C10 alkyl, a straight or branched C1 to C10 alkanol, a phenyl, and a benzyl.

In another embodiment of item (5), said substrate compound of formula FI is selected from the group consisting of S-benzyl-Cys-Gly, O-benzyl-Ser-Gly, (1-(2-hydroxyethyl)-1-methylbutyl)-L-cysteinyl-glycine, S-benzyl-Cys-Ala, O-benzyl-Ser-Ala, Pro-Gly, Ala-Gly, Ala-Ala, and Pro-Ala.

In yet another embodiment of item (5), said substrate compound of formula FI is selected from the group consisting of S-benzyl-Cys-Gly, O-benzyl-Ser-Gly, (1-(2-hydroxyethyl)-1-methylbutyl)-L-cysteinyl-glycine, S-benzyl-Cys-Ala, O-benzyl-Ser-Ala.

In yet another embodiment of item (5), said substrate compound of formula FI is selected from the group consisting of Pro-Gly, Ala-Gly, Ala-Ala, and Pro-Ala.

(6) A method of inhibiting the peptidase as defined herein, in particular under item (1), in its ability to cleave its substrate wherein the peptidase is contacted with a peptidase inhibitor.

(7) The method of item (6) for preventing or reducing the formation of body malodour wherein an inhibitor of a peptidase is applied to a body surface, and wherein the peptidase is a peptidase as described herein, in particular, without limitation, under item (1).

(8) The method of item (7) wherein the compound is applied in form of a dermatologically acceptable composition comprising at least one excipient.

(9) A method for preparing a personal care product having an effect against body malodour formation wherein an inhibitor of a peptidase is added to a personal care product formulation, and wherein the peptidase is a peptidase as described herein, in particular, without limitation, under item (1).

(10) A composition comprising a peptidase substrate and an isolated peptidase,
wherein the peptidase is the peptidase as described herein, in particular, without limitation, under item (1);
wherein the peptidase substrate is the peptidase substrate as described herein, in particular under any one of items (2) or (3) or any one of their particular embodiments.

(11) The composition of item (10) wherein the peptidase is in a form selected from the group consisting of in isolated form, in form of a preparation containing functional peptidase, in form of heterologous expression in a suitable host cell, in form of Corynebacterium jeikeium expressing the peptidase, and in form of Corynebacterium jeikeium K411 expressing the peptidase.

(12) An isolated peptidase wherein the peptidase is the peptidase as herein described, in particular, without limitation, as described under item (1),
and wherein the peptidase is homologous to a sequence selected from SEQ ID NO:2 and SEQ ID NO: 4 with a sequence identity of at least 40%.

(13) The isolated peptidase of item (12) wherein the peptidase is homologous to a sequence selected from SEQ ID NO:2 and SEQ ID NO: 4 with a sequence identity of at least 80%.

In other embodiments, the sequence identity is at least 85%, at least 90%, at least 95%, or at least 98%.

(14) A nucleotide encoding a peptidase wherein the peptidase is as the peptidase as described herein, in particular, without limitation, under item (1), which is selected from the group consisting of
a nucleotide substantially homologous to a nucleotide sequence of SEQ ID NO:1 as determined by sequence identity,
a nucleotide which is a conservatively modified variant of SEQ ID NO:1 not causing aminoacid changes when translated into the corresponding protein,
a nucleotide substantially homologous to SEQ ID NO:1 as determined by hybridisation,
wherein the substantially homologous nucleotide as determined by sequence identity has a sequence identity of at least 80%.

In other embodiments, the sequence identity is at least 85%, at least 90%, at least 95%, or at least 98%.

(15) The isolated nucleotide of item (16) wherein said isolated nucleotide forms part of an expression vector.

(16) The isolated nucleotide of item (16) wherein the expression vector forms part of a host cell transfected with the expression vector.

(17) A method of forming a peptidase comprising the step of culturing host cells comprising an expression vector encoding for the peptidase under conditions sufficient for expression, thereby forming the peptidase and optionally recovering it from the cells, wherein the peptidase is the peptidase as herein described, in particular, without limitation, as described under item (1).

DETAILED DESCRIPTION

The following passages describe in detail the peptidase and its variants, its substrates, its reaction products, its use in the identification of modulators and inhibitors of body malodour including various screening assays and how to perform them, including the cells that may be used, assays using purified peptidase, peptidase transcription assays, expression systems for peptidase, overexpression of peptidase, transfection of peptidase constructs into cells, peptidase protein recovery, modulators of peptidase, the identification of peptidase substrates, binding assays, kit to identify a modulator, Confirmation of identified modulators, large scale screening assays, libraries of test agents, types of test agents, personal care products and peptidase sequences.

Peptidase and Substantially Homologous Sequences:

The peptidases (or nucleotides encoding them) useful in methods described herein may be selected from the group consisting of the peptidase of SEQ ID NO:2 (or SEQ ID NO:1 for the nucleotide encoding it), the peptidase of SEQ ID NO: 4 (or SEQ ID NO:3 for the nucleotide encoding it), and peptidases that are substantially homologous to SEQ ID NO:2 and/or SEQ ID NO:4 (or SEQ ID NO:1 and/SEQ ID NO:3 for the nucleotides encoding them) and remain functional, i.e. the peptidase binds to a substrate/malodourant precursor as herein-described and/or reacts/cleaves said substrate/malodourant precursor (or in case of the nucleotides they are considered functional if they code for such a peptidase). For example, without limitation, a peptidase or nucleotide encoding a peptidase which is derivable from *corynebacteria* naturally occurring in or isolatable from the human axilla.

A substantially homologous peptidase comprises the following blocks of conserved partial sequences (the letters refer to the single character aminoacid code and X is any one of the common aminoacids, and said aminoacids are numbered starting from the N-terminus of the substantially homologous peptidase in its naturally occurring form:

ERDGRWYGRGXADCKG between aminoacid 105 and 150,
EGSEEXG between aminoacid 150 and 180,
HSGXXGGXAPDA between aminoacid 205 and 255,
GGSIPL between aminoacid 385 and 425.

For numbering, either the naturally occurring sequence of the substantially homologous peptidase is used, or, before numbering, as will be apparent to the skilled person, any added tags, fused sequences, or similar are corrected and not considered in the numbering of the sequence so as to number it consistent with the sequence in its naturally occurring form, i.e. without such or similar changes that will affect the numbering.

The conserved sequence blocks are also shown in the figure below.

The identified peptidase enzymes SEQ ID NO:2 and SEQ ID NO:4 were isolated from *Corynebacterium* sp. Ax20 (SEQ ID NO:2) and *Corynebacterium jeikeium* (SEQ ID NO:4), more particularly from *Corynebacterium* sp. Ax20, DSM 14267, most closely related to *Corynebacterium striatum* or *glaucum*, which has been submitted on the 26, April 2001 to the International Depository Authority DSMZ-German Collection of Microorganisms and Cell Cultures, D-38124 Braunschweig (Accession Number DSM 14267), and *Corynebacterium jeikeium* K411 (Tauch et al. 2005, J. Bacteriol. 187(13): 4671-82).

Ax20 (DSM 14267) was isolated from human axilla and is most closely related to *Corynebacterium striatum* according biochemical tests (API Coryne test kit, BioMerieux, France), based on sequence analysis of the full 16S rRNA gene, it is most closely related to type strains from the species *Corynebacterium glaucum*.

*Corynebacterium jeikeium* is known for opportunistic infections, especially in immunocompromised patients. K411 was isolated from the human axilla. It is a lipid-requiring and multidrug-resistant bacterial species of the human skin flora that has been recognised as a nosocomial pathogen.

The term peptidase or peptidases as used herein may refer to the Ax20 peptidase (SEQ ID NO:2), the K411 peptidase (SEQ ID NO:4), or peptidases substantially homologous thereto as described herein.

The peptidases were classified as metallopeptidases insofar as they require the presence of Zn ions as a cofactors. They are functionally related to the previously identified metallopeptidase (AMRE) that releases unsaturated or hydroxylated acid malodourants, and is also zinc-dependent. The nucleotide sequences encoding the peptidases have been isolated and sequenced (SEQ ID NO:1, SEQ ID NO:3). Each peptidase gene sequence can be introduced in a suitable expression vector and used to produce the peptidase by heterologous expression in the desired microorganism or cells.

Sequences SEQ ID NO: 1 and 2 (from Ax20) were not previously described, and the isolated peptidase of SEQ ID NO:4 has not been previously described.

In vivo, the peptidases occur intracellularly and can be released from the cells by mechanical disruption of the cell envelope. Thus, the peptidase may be isolated from cellular extracts, in particular cellular extracts obtained from cells derived from organisms selected from the group consisting of wild-type corynebacteria strains.

The *corynebacteria* include, for example, without limitation, *Corynebacteria* sp., *Corynebacterium striatum*, *Corynebacterium glaucum*, *Corynebacterium jeikeium*, FIG. 2 Sequence alignement of SEQ ID NO: 2 and SEQ ID NO: 4 showing the conserved sequence blocks

```
CoryAx20    113  ERDGRWYGRGAADCKG NVIMHLEALRMVQEN------GGTDLGLKVVM EGSEELGG EDGL
CoryJeke    119  ERDGRWYGRCTADCKG HVAMHVAVLRALSIL SDAHFPAAKNLGIRIVV EGSEERGG -YGL
consensus        ERDGRWYGRG ADCKG  V MH1   LR v      sdahfpgg LGlkvVm EGSEE GG  e GL CoryAx20    167  GKLIDANPELFTADVIPFIGDGGNVAVGIPPLTIHLRGGAQLRFKVDTLEGLY HSGWGGA
CoryJeke    178  EDLLAEKPELRAADTFLIADSGNDALGEPLLCIALRGSAPVTVPTRILAQEM HSGQFGGS
consensus         Li   PELF AD   IgD GN AvG PtL T LRG A l   k   TL   Pv HSG wGG CoryAx20    227  APDA AHALIRITDSFFDBHGRTTIECVDTTAKVECDPYDRETFRKDARVLDGVQLLGTVD
CoryJeke    238  APDA LVELVQLLSTLHDENGLVAVPGLEPKEPWGEVGPTEQEFRDNAGVTDGVELYGAGE
consensus        APDA    Li ii s   DE G    i Gvd    kW G        FR  A V DGV L G  d CoryAx20    287  DELADMVWARPALTVIGFTSVPVEDATNIVNPTAEAQFNLRVEAPQSAAEVAKKVEEQIR
CoryJeke    298  WQENDLTVMNESTIITGLDALSVADSVNSVPAIAAAVVSLRVEPGREPQECQDLLVKHLE
consensus            P Dm    P ITv G   v V D  N V  TA A    LRVP    E   v   i CoryAx20    347  ARAPWGAKVEVSITGVNEPESTDPNGPAVQHFGKCLQDAYGABHLTVVGT GGSIPL IVTL
CoryJeke    358  SQKTN-ALVEIERGSLADAEQATSGPALQPLGEALGEVYGKETMEVA-G GGSIPL INKL
consensus            gA VEv   v  E  F  D  GPAvQh G  L d YG E l V gt GGSIPL  T   L
```

*Corynebacterium* sp. Ax 20, *Corynebacterium jeikeium* K411, *Corynebacterium xerosis*, *Corynebacterium appendicis*, *Corynebacterium coyleae*, *Corynebacterium mucifaciens*, *Corynebacterium riegelii*, and *Corynebacterium tuberculostearicum*.

A good source of wild-type corynebacteria strains is the human axilla, from which bacterial strains may be cultured and isolated, as is well known in the art.

All of the above corynebacteria were isolated from or occur in the human axilla, express malodour forming enzymes and are able to form malodour.

Peptidase may be used in form of intact cells, or in isolated form, for example as a crude extract, or in purified form. For example, a crude extract may be formed by mechanical disruption of the cells. Optionally peptidase may be purified. Alternatively peptidase may be formed recombinantly as described herein.

A substantially homologous peptidase protein includes such proteins where the substrate binding and/or catalytic part is replaced with the relevant part of an allelic variant from a different species, for example another human axilla derived bacterium including but not limited to bacteria of the genus *Corynebacterium*.

Further, substantially homologous peptidase nucleotide or polypeptide sequences may be formed by conservative mutations and/or point mutations and include any conservatively modified variant as detailed below.

With respect to nucleotide sequences, conservatively modified variants means nucleotides which encode identical or essentially identical amino acid sequences (conservatively substituted amino acids, i.e. lysine switched to arginine and further examples as explained herein-below).

Because of the degeneracy of the genetic code, a large number of nucleotides different in sequence but functionally identical encode any given polypeptide/protein. Such nucleotide variations are "silent variations," which are one species of conservatively modified variations. Each nucleotide sequence which encodes a polypeptide also describes every possible silent variation of the nucleotide. Therefore, each codon in a nucleotide (except AUG, which is ordinarily the only codon for methionine, and TGG, which is ordinarily the only codon for tryptophan) can be modified to yield a functionally identical nucleotide sequence that will produce an identical polypeptide. Accordingly, each silent variation of a nucleotide which encodes a polypeptide is implicit in each given nucleotide sequence.

With respect to amino acid sequences, amino acid substitutions may be introduced using known protocols of recombinant gene technology including PCR, gene cloning, site-directed mutagenesis of cDNA, transfection of host cells, and in-vitro transcription which may be used to introduce such changes to the peptidase sequence. The variants can then be screened for peptidase activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gin or glu; met/leu or tyr or ile; phe/met or leu or tyr; ser/thr; thr/ser; trp/tyr; tyr/trp or phe; val/ile or leu.

An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (1); 5) Isoleucine (I), Leucine (L), Methionine (M), Valine (V); and 6) Phenylalanine (F), Tyrosine (Y), Tryptophan (W).

Another alternative guideline is to allow for all charged amino acids as conservative substitutions for each other whether they are positive or negative.

In addition, individual substitutions, deletions or additions that alter, add or delete a single amino acid or a small percentage (for example up to 26%, or up to 20%, or up to 10%) of amino acids in an encoded sequence are also considered to be conservatively modified variations.

Substantially homologous nucleotide or polypeptide sequences have the degree of sequence identity indicated below while retaining the catalytic activity of the polypeptide on the substrates as defined herein.

% Sequence identity:

A substantially homologous nucleotide sequence has a % sequence identity of at least at least 50%, at least 55%, at least 60%, at least 70%, at least 80%, at least 90%, at least 95%, or at least 98%.

A substantially homologous polypeptide sequence has a % sequence identity of at least at least 40%, at least 42%, at least 50%, at least 60%, at least 70%, at least 80%, at least 90%, at least 95%, or at least 98%

Notably, when comparing the peptidase Ax20 (SEQ ID NO:1 and NO:2) and peptidase K411 (SEQ ID NO:3 and NO:4), which both have the same catalytic activity on the same physiological substrate, based on their aminoacid sequence, their identity is 42%, and based on their nucleotide sequences, their identity is 55%.

Calculation of % Sequence Identity is determined as follows.

BLAST (Basic Local Alignment Search Tool) is the heuristic search algorithm employed by the programs blastn which is available at http://www.ncbi.nlm.nih.gov.

To determine % identity of a nucleotide query sequence against another nucleotide sequence, Blastn is used, using default parameters of BLAST version 2.2.1.3, including an EXPECT (statistical significance threshold for reporting matches against database sequences) of 10, and DUST filtering.

To determine % identity of a polypeptide query sequence against another polypeptide sequence, Blastp is used, using default parameters of BLAST version 2.2.1.3, including an EXPECT of 10, and DUST filtering.

Substantially homologous nucleotide sequences include, without limitation, sequences that are selectively hybridising to one or more of the peptidase nucleotide sequences described herein, or to their complement, under stringent hybridisation conditions detailed below. Stringent conditions are temperature of 42° C. in a solution consisting of 50% formamide, 5×SSC, and 1% SDS and washing at 65° C. in a solution consisting of 0.2×SSC and 0.1% SDS (1×SSC=0.15 M NaCl, 0.015 M Na3 Citrate pH 7.0).

Background hybridisation may occur because of other nucleotide sequences present, for example, in the genomic DNA library being screened.

A signal that is 2 fold less intense or optionally 10 fold less intense than the specific interaction observed with the target DNA is considered background. The intensity of interaction may be measured, for example, by radiolabeling the probe, e.g. with 32P.

The term "isolated" as used herein means taken from the environment that something originated from and transferred to a different environment, including the environment of an intact cell and transferring it to a cell lysate.

By "purified form", is meant more than 80%, for example, without limitation, more than 90%, more than 95%, more than 98%, more than 99% or more with respect to other protein and/or nucleic acid contaminants (w/w).

Substrates of Peptidase

The substrates of the peptidase (for example, without limitation, precursor I) may generally be described as dipeptide derivatives. Examples of substrates include, without limitation, simple dipeptides such as ala-ala and ala-gly. The substrates with the highest affinity to the peptidase are cys-gly and cys-ala derivatives, in particular L-cys-L-gly and L-cys-L-ala derivatives wherein the S atom of the cys-gly or cys-ala residue is alkylated as described herein.

The cys-gly derivatives can be the naturally occurring, for example, without limitation, precursor I, or synthetic analogues including but not limited to S-benzyl-Cys-Gly.

Whether a given dipeptide derivative is a peptidase substrate may be easily determined by incubating it with the SEQ ID NO: 2 or SEQ ID NO:4 peptidase and determining whether said substrate is enzymatically reacted by the peptidase as described herein.

Substrates include, without limitation, substrates with high affinity to the enzyme which may be of formula FI shown below

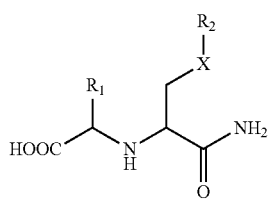

FI and wherein X is selected from the group consisting of S and O, and wherein R1 is a residue selected from the group consisting of H and methyl, and wherein R2 is a residue selected from the group consisting of a straight chain or branched C1 to C10 alkyl, a straight chain or branched C1 to C10 alkanol, a phenyl, and a benzyl.

A particular group of useful substrates are the substrates of formula FI wherein X is S, R1 is methyl, and R2 is a residue selected from the group consisting of a straight chain or branched C1 to C10 alkyl, a straight chain or branched C1 to C10 alkanol, a phenyl, and a benzyl.

With regard to R2 residues, "C1 to C10 alkyl" includes, without limitation, methyl, ethyl, propyl, butyl, pentyl, hexyl, heptyl, octly, nonyl, and decyl; and "C1 to C10 alkanol" includes, without limitation, methanol, ethanol, propanol, butanol, pentanol, hexanol, heptanol, octanol, nonanol, decanol, and optionally any branched forms of alkyl or alkanol.

Physiologically relevant substrates are those indicated herein-above as "precursor I" and have the general formula FII

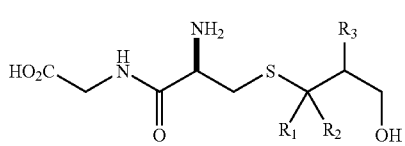

FII wherein R1 is an alkyl residue selected from the group consisting of methyl, ethyl, propyl, butyl, pentyl, and hexyl, and wherein R2 and R3 are independently selected from the group consisting of H and methyl.

Particular examples of peptidase substrates include, without limitation, S-benzyl-Cys-Gly, O-benzyl-Ser-Gly, (1-(2-hydroxyethyl)-1-methylbutyl)-L-cysteinyl-glycine, S-benzyl-Cys-Ala, O-benzyl-Ser-Ala, Pro-Gly, Ala-Gly, Ala-Ala, Pro-Ala. Their chemical structures are shown in the table below.

| | |
|---|---|
| S-benzyl-Cys-Gly | 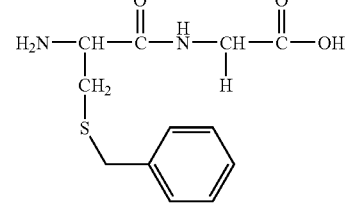 |
| O-benzyl-Ser-Gly | 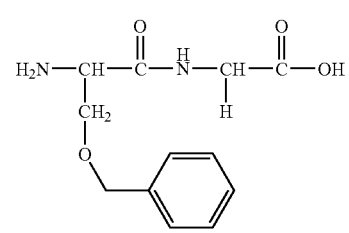 [SMILES: NC(COCc1ccccc1)C(=O)NCC(=O)O] |
| (1-(2-hydroxyethyl)-1-methylbutyl)-L-cysteinyl-glycine | 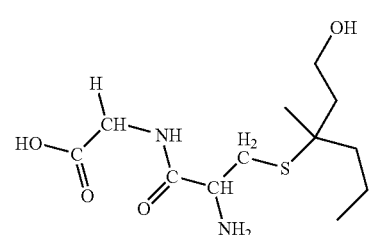 |
| S-benzyl-Cys-Ala | 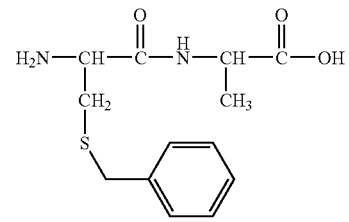 [SMILES: CC(NC(=O)C(N)CSCc1ccccc1)C(=O)O] |
| O-benzyl-Ser-Ala | 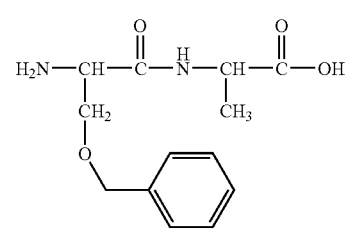 |
| Pro-Gly | 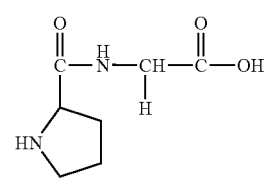 [SMILES: O=C(O)CNC(=O)C1CCCN1] |

-continued

Ala-Gly
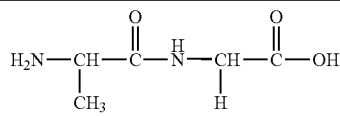

Ala-Ala
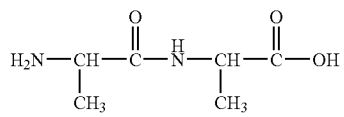

Pro-Ala
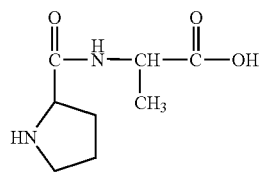

Peptidase Reaction Products:

The products of an enzymatic reaction with peptidase are two free amino acids for the simple dipeptide substrates or for gly derivatives, a free glycine and a S-substituted cys or an O-substituted ser derivative, or for ala derivatives, a free alanine and a S-substituted cys or an O-substituted ser derivative.

The final malodourant product is only formed when the resulting enzymatic reaction product of peptidase (for example, precursor II) is exposed to a β-lyase by which it is cleaved to release a sulfanylalkanol.

The novel constructs and products that are provided (DNA, vectors, recombinant bacteria, protein/peptidase enzyme) are useful when screening, without limitation, for inhibitors of the peptidase reaction.

Identification of Modulators and Inhibitors:

Modulators which are inhibitors are of interest to add to products (in particular to personal care products including but not limited to deodorants) to prevent the formation of body malodour. Similarly, the screening methods described herein below could be used to identify other modulators such as enhancers, which are to be avoided in such products.

To identify a modulator, the peptidase and its substrate are exposed to at least one test agent (potential modulator) in a suitable concentration, for example, without limitation, from 1 nm to 1 mM, or from 10 nm to 10 microM.

Then the effect of the modulator on the enzymatic cleavage/reaction rate is monitored by methods well known in the art, for example, without limitation, by methods as described herein.

A change of the enzymatic cleavage/reaction rate is determined by the educt cleavage rate or product formation rate (the latter includes secondary products).

For example, the cleavage/reaction rate is determined by monitoring the rate that the substrate disappears, or the rate that cleavage products of the substrate appear (for example, the rate that the free aminoacid reaction product appears, including but not limited to gly or ala).

In one embodiment of a high-throughput screen of potential modulators, the release of free L-gly or L-ala is measured by derivatising the free Na group with an amine-group derivatising agent, which upon reaction with the amine group forms a chromophore or a fluorescent molecule. Useful in this regard may be the use of fluorescamine (Fluka, Buchs, Switzerland) to form a fluorescent molecule upon reaction with L-gly or L-ala. Finally, the cleavage of the L-gly-substrate may be compared to control reactions and the potential of the test compounds to influence, in particular to inhibit, the reaction may thereby be quantified.

If the β-lyase or another enzyme acting on the peptidase reaction product is added to the reaction as well, then alternatively or additionally, the rate by which the malodourant (sulfanylalcohol) or other released sulfur molecules appear can be monitored. A change in the monitored rate indicates the effect of a test agent and potential modulator on the enzyme. An inhibitor is identified by a lower rate of cleavage product formation or lower rate of free amino acid release or lower rate of sulfur molecule formation when compared to the reaction in absence of the inhibitor test agent or a pre-determined standard rate.

The cleavage/reaction rates can be monitored, for example, without limitation, by the following methods: analysis of the substrate or the formed free amino acids or other cleavage products by high performance liquid chromatography (HPLC) or thin layer chromatography (TLC) or capillary electrophoresis; fluorescence spectrophotometry after reacting the free amino acid with a fluorescent probe (for example, without limitation, fluorescamine); fluorescence spectrophotometry after reacting the free sulfur molecule with a fluorescent probe (for example, without limitation, monobromobimane); gas chromatography of released sulfur molecules; or the detection of reaction products by biochemical tests.

Useful peptidases include, without limitation, the peptidase of SEQ ID NO:2 and the peptidase of SEQ ID NO:4. The peptidase of SEQ ID NO:4 has a lower activity then the peptidase of SEQ ID NO:2 but is still very useful as a screening target or to verify screening hits and/or to screen for a broad range activity of inhibitors in different bacterial species.

These screens can be performed subsequently or in parallel, using both enzymes in one reaction well.

In parallel or subsequently to the screening methods employing peptidase as described herein, additional malodour-forming enzymes can be used, for example, without limitation, one or more of β-lyase and AMRE. To that end, β-lyase and/or AMRE may be incubated with the peptidase and its substrate and the test agent in parallel or subsequently and the effect of the test agent on the cleavage/reaction rate of the enzymes is determined by the change in formation of a sulfanylalkanol (released by peptidase and 3-lyase) and/or carboxylic acids or glutamine (released by AMRE). Alternatively, the change in the reaction rate of the educts of the reaction may be determined.

Identified inhibitors of one or more of peptidase SEQ ID NO:2, peptidase SEQ ID NO:4, and substantial homologs are desirable deodorant ingredients since they inhibit the rate limiting step in releasing sulfur chemicals from odourless sweat. Particularly interesting are inhibitors which inhibit more than one corynebacterial peptidase, for example, without limitation, both peptidase SEQ ID NO:2 and peptidase SEQ ID NO:4, and therefore will provide a broad band activity against a number of different *corynebacteria* species.

The results in the examples herein-below show that β-lyase cleaves only the cys-conjugate but not precursor I of FIII, indicating that the β-lyase alone cannot be responsible for the cleavage of the quantitatively most abundant substrate in the axilla secretion. In contrast, the peptidase-containing extract from *C. sp.* Ax 20 isolated from the axilla of a human test subject does release sulfanylalkanol malodourants from precursor I of FIII (in the examples: cys-gly conjugate) and this reaction is stopped by the metallopeptidase inhibitor o-phenantrolin. This is surprising since WO 2006079934 postulates a β-lyase cleaving precursor I of FIII. It follows that the cell extracts contain another enzyme than a β-lyase that is involved in the cleavage of precursor I of FIII. But since no single fraction of the cell extract of Ax20 can release the malodourant sulfur volatile from precursor I of FIII as shown in the examples herein and since a single fraction in presence of beta-Lyase can release the malodourant sulfur volatile from precursor I of FIII, again, as shown in the examples herein, it follows, that two enzymes sequentially release the malodourant from precursor I of FIII, namely a peptidase releasing gly, and thereby forming the substrate for the beta-lyase which in turn releases the sulfur molecule.

Cells Used in the Assays:

Suitable bacterial cells include all *corynebacteria* that naturally express peptidase, for example, without limitation, *Corynebacterium* sp., *Corynebacterium* sp. Ax20, *Corynebacterium striatum*, *Corynebacterium glaucum*, *Corynebacterium jeikeium*, *Corynebacterium jeikeium* K411, *Corynebacterium xerosis*, *Corynebacterium appendicis*, *Corynebacterium coyleae*, *Corynebacterium mucifaciens*, *Corynebacterium riegelii*, and *Corynebacterium tuberculostearicum*.

Alternatively the peptidase may be heterologously expressed in a host strain, for example, without limitation, a bacterial strain (including, without limitation, an *E. coli* strain), a yeast strain, or an eukaryotic cell line (including, without limitation, insect cells, mammalian cells, amphibian cells, and worm cells). These host strains are transformed with a suitable vector carrying the nucleotide sequence coding for the peptidase and the relevant control elements for the host, as is well known in the art.

The vector constructs for expressing the peptidase may be produced in a manner known per se using polymerase chain reaction (PCR) to amplify the coding region from chromosomal DNA of a *corynebacterium* and, after verification of the sequence, sub-cloning the coding sequence into a suitable vector. Suitable vectors are commercially available, for example vectors from Invitrogen (Groningen, The Netherlands). A useful vector is the vector pET-3a (Studier and Moffatt, 1986). The resulting plasmids are transformed into a suitable *E. coli* host strain. Suitability of a vector-host strain combination depends on the chosen host-strain for which a vector is compatible with or optimized for (for example the vector pET-3a is transformed into the host strain BL21 (DE3)).

Alternatively, a variety of expression vector/host systems can be used to contain and express sequences encoding the peptidase. These include, for example, different microorganisms including bacteria transformed with recombinant bacteriophage, plasmid, or cosmid DNA expression vectors; yeast transformed with yeast expression vectors; insect cell systems infected with viral expression vectors (for example baculovirus), or with bacterial expression vectors (for example pBR322 plasmids).

Yeast expression systems may be used for production of peptidase. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation.

For the expression of heterologous proteins in insect cell lines is, for example, derivatives of the Lepidopteran baculovirus, *Autographa californica* multicapsid nucleo-virus (AcMNPV) can be used. In this system, foreign gene expression is directed by a very strong late viral promoter, either the polyhedrin or p10 promoters, and a wide array of vectors is available that optimises expression and recovery of recombinant proteins. These vectors enable expression of both membrane-bound and secreted proteins at high levels. A number of vectors are commercially available, for example the Insect-Select™ System from Invitrogen.

Assays Using Purified Peptidase:

Alternatively to using a cell-based assay, it usually will be simpler to purify the peptidase from peptidase expressing cells described herein-above using methods well known in the art and subsequently performing an enzymatic assay contacting the purified peptidase, its substrate and a test agent in vitro and determining a change in the peptidase reaction rate as described herein. Optionally, the results may be validated in vivo using *corynebacteria* derivable from the human axilla as described herein.

Peptidase Transcription Assays:

Alternatively to cell-based or enzymatic assays, an assay to identify modulators that act on the level of gene transcription may be performed. Test agents are added to peptidase expressing wildtype *corynebacteria*. After a finite time (for example, 30 min to 8 h) the test agents are removed by washing the bacterial cells or by harvesting the cells by centrifugation. The bacterial cells are then analyzed for the amount of the peptidase, and this value is compared to control cells not exposed to the test agent. Inhibitors reduce the amount of peptidase formed by the bacteria and therefore their potential to form malodour. The amount of peptidase of the bacterial cells can be determined either by an activity assay using the methods and substrates as described herein or by raising a specific antibody (either a monoclonal antibody or a polyclonal antibody) to a peptidase including, without limitation, SEQ ID 2 or SEQ ID 4 and then using a suitable immunological detection method, for example, without limitation, immuno dot-blot, western-blot, or enzyme-linked immunosorbent assay (ELISA), to specifically detect the peptidase in the bacterial cells.

Expression Systems for Peptidase:

In order to express cDNAs encoding the desired proteins, one typically subclones the appropriate cDNA into an expression vector that contains a strong promoter to direct transcription, a transcription/translation terminator, and a ribosome-binding site for translational initiation. Suitable bacterial promoters are well known in the art, for example, *E. coli*, *Bacillus* sp., and *Salmonella*, and kits for such expression systems are commercially available. Similarly, eukaryotic expression systems for mammalian cells, yeast, and insect cells are commercially available. The eukaryotic expression vector may be, for example, an adenoviral vector, an adeno-associated vector, or a retroviral vector.

An expression cassette should also contain a transcription termination region downstream of the structural gene to provide for efficient termination. The termination region may be obtained from the same gene as the promoter sequence or may be obtained from different genes.

For expression of the proteins, conventional vectors for expression in eucaryotic or procaryotic cells well known in the art may be used. Examples of vectors include bacterial expression vectors, for example, plasmids including pBR322-based plasmids, pBAD base plasmid, pSKF, and pET23D, and fusion expression systems, for example, GST and LacZ.

Expression vectors containing regulatory elements from eukaryotic viruses are typically used in eukaryotic expression vectors, for example SV40 vectors, cytomegalovirus vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, pcDNA3.1, pIRES and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, dihydrofolate reductase and the like. The elements that are typically included in expression vectors may also include a replicon that functions in *E. coli*, a gene encoding drug resistance to permit selection of bacteria that harbor recombinant plasmids, and unique restriction sites in non-essential regions of the plasmid to allow insertion of eukaryotic sequences. The particular drug resistance gene chosen is not critical, any of the many drug resistance genes known in the art are suitable. The prokaryotic sequences are optionally chosen such that they do not interfere with the replication of the DNA in eukaryotic cells, if necessary.

In bacterial systems the peptidase cDNA fragment may be expressed alone or as a fusion protein wherein the peptidase protein of interest is fused to the *E. coli* periplasmic maltose-binding protein (MBP) wherein the MBP, including its signal peptide, is linked to the amino terminus of the peptidase. The wild-type peptidase cDNA or the MBP: peptidase fusion cDNA is subcloned into a suitable plasmid, for example pBR322, where in *E. coli*, peptidase expression is driven by the lac wild-type promoter.

Particular examples of vector-host strain combinations are the vector pPROTet.E133 in strain *E. coli* DH5αPRO (Clontech, Palo Alto, Calif., USA) or the vector pBAD-myc-his-A in *E. coli* strain TOP 10 (Invitrogen, Groningen, The Netherlands).

Further examples of expression vectors and host strains are described in T. Maniatis et al. (Molecular Cloning, cold spring Harbor Laboratory, 1982).

In vitro transcription and translation is another alternative to express peptidase.

Overexpression of Peptidase:

Peptidase may be overexpressed by placing it under the control of a strong constitutive promoter, for example the CMV early promoter. Alternatively, overexpression may be achieved under control of an inducible promoter, for example, without limitation, the arabinose promoter in the vector pBAD-myc-his-A or the T-rex system described herein below.

Transfection of Peptidase Expression Vector Constructs into Cells:

Standard transfection methods can be used to produce bacterial, mammalian, yeast or insect cell lines that express large quantities of the protein.

Any known method for introducing nucleotide sequences into host cells may be used. It is only necessary that the particular genetic engineering procedure used be capable of successfully introducing the relevant genes into the host cell capable of expressing the proteins of interest. These methods may involve introducing cloned genomic DNA, cDNA, synthetic DNA or other foreign genetic material into a host cell and include the use of calcium phosphate transfection, polybrene, protoplast fusion, electroporation, liposomes, microinjection, plasma vectors, viral vectors and the like.

For example, without limitation, the T-Rex™ expression system (Invitrogen Corp., Carlsbad, Calif.) may be used. The T-Rex™ System is a tetracycline-regulated mammalian expression system that uses regulatory elements from the *E. coli* Tn10-encoded tetracycline (Tet) resistance operon. Tetracycline regulation in the T-Rex™ System is based on the binding of tetracycline to the Tet repressor and depression of the promoter controlling expression of the gene of interest.

After transfection, the transfected cells may be cultured using standard culturing conditions well known in the art. It will be apparent to the skilled person that different cells require different culture conditions including appropriate temperature and cell culture media.

Peptidase Protein Recovery:

If desired, the protein may be recovered from the cells using standard techniques. For example, the cells may be burst open either mechanically or by osmotic shock. The resulting crude enzyme may be used as such or may be separated from one or more of cell debris, cell proteins, cell nucleic acids, and cell contaminants, for example by being subjected to precipitation and chromatography steps, including but not limited to ion-exchange, hydrophobic interaction, reverse-phase, and size exclusion chromatogrphy steps. After each step the eluted protein may be further purified and/or concentrated by methods including but not limited to filtration and ultrafiltration. Alternatively, the recombinant protein may be recovered from the culture medium in which the recombinant cells had been cultured (provided the peptidase has been expressed together with a sequence that provides for export into the culture medium).

Modulators that May be Identified by the Assays:

Modulators and in particular inhibitors of peptidase activity can be identified as described herein below.

There now follows a definition of the agents to be identified in the methods described herein.

A modulator is an agent that effects an increase or decrease of one or more of the following: the binding of a substrate to the peptidase, the reaction of the substrate (for example, without limitation, a malodourant precursor) to the malodourant or a second malodourant precursor. The modulator can itself bind to the peptidase, either at the substrate binding site or elsewhere, and can either be cleaved or reacted at a different rate or not at all, or can bind to the substrate and thereby affect its reaction/cleavage rate.

Modulators include various types of compounds, including small molecules, peptides, proteins, nucleotides, antibodies or fragments thereof. These can be derived from various sources including synthetic or natural, extracts of natural material, for example from animal, mammalian, insect, plant, bacterial or fungal cell material or cultured cells, or conditioned medium of such cells.

A substrate is an agent that binds to the peptidase and is cleaved or reacted by it.

An inhibitor is a modulator that decreases the binding of a substrate to the peptidase as compared to the binding of the substrate in the absence of inhibitor, and/or decreases the reaction/cleavage rate of the substrate, and/or decreases overall peptidase activity.

An enhancer increases the binding of a substrate to the peptidase as compared to the binding of the substrate in the absence of enhancer, and/or increases the reaction/cleavage rate of the substrate, and/or increases overall peptidase activity.

The activity, or changes in activity, of a peptidase binding a substrate and reacting/cleaving it to form a second precursor and finally the malodourant can be determined by the methods described herein-below.

Identification of Substrates:

To identify a substrate, a test agent is incubated with peptidase and the formation of reaction products or the disappearance of the potential substrate is followed by analytical methods as described herein. Any compound which is reacted by the peptidase is defined as a substrate. To rate the affinity of a substrate versus other known substrates, dilution series of the substrate are incubated with a fixed concentration of peptidase, and the cleavage rate at each substrate concentration after a given time is determined. Based on the resulting curve, the biochemical parameters $v_{max}$ (maximal reaction rate in molecules substrates cleaved per second by one molecule of peptidase) and $K_m$ (Michaelis constant giving the substrate concentration where the enyme is active with 50% of maximal reaction rate) are determined. A low $K_m$ indicates a high affinity of the peptidase for its substrate and thus a substrate with a low $K_m$ and a high $v_{max}$ is a particularly good substrate for the enzyme. However, for screening assays, substrates with a high Km and low $v_{max}$ may also be used.

Kit to Identify a Modulator:

A kit, for example a screening kit or high throughput screening kit, that comprises isolated peptidase (from wild-type or recombinant cells) or recombinant cells that express the peptidase, or a substantially homologous sequence thereto; and that comprises a substrate of the peptidase, for example, without limitation, S-benzyl-Cys-Gly, O-benzyl-Ser-Gly, (1-(2-hydroxyethyl)-1-methylbutyl)-L-cysteinyl-glycine, S-benzyl-Cys-Ala, O-benzyl-Ser-Ala, Pro-Gly, Ala-Gly, Ala-Ala, Pro-Ala.

The substrate is provided in suitable concentrations, for example 1 microM to 10 mM, or 10 microM to 1 mM, for example 50 microM to 1 mM, or 50 microM to 500 microM.

Optional kit components may include a suitable medium for culturing the recombinant cells provided, and a culture device to grow the cells in, for example, a microtiter plate, these optional components will be readily available to the skilled person.

The kit may be used as follows:
(i) growing recombinant cells that express the peptidase, or alternatively, providing an isolated peptidase,
(ii) adding at least one test agent in the presence of a peptidase substrate in a suitable concentration, and
(iii) determining a change in cleavage/reaction rate of the substrate/its product(s) by the peptidase or a change in substrate binding to the peptidase by comparing the response in presence and absence of the test agent, and the test agent is thereby identified as a modulator.

In particular, for the kit using isolated peptidase:
(i) test agents, optionally at concentrations from about 1 nanomolar to about 5 millimolar, are added to a peptidase containing assay buffer,
(ii) after a defined pre-incubation period which allows test agent binding to the peptidase (optionally, 0 to 15 minutes), the selected substrate is added in a suitable concentration,
(iii) a change in cleavage/reaction rate of the substrate or its product(s) by the peptidase or a change in substrate binding to the peptidase is determined by comparing the response in presence and absence of the test agent, and the test agent is thereby identified as a modulator.

A similar assay can be performed where the peptidase is not in an isolated form but in the form of a cellular extract or is provided in form of intact prokaryotic or eucaryotic cells:
(i) recombinant cells that express the peptidase protein are grown in culture,
(ii) test agents, optionally at concentrations from about 1 nanomolar to 5 millimolar, are added to the culture medium in the presence of the substrate in a suitable concentration,
(iii) a change in cleavage reaction rate of the substrate or its product(s) by the peptidase or a change in substrate binding to the peptidase is determined by comparing the response in presence and absence of the test agent, and the test agent is thereby identified as a modulator.

For example, without limitation, step (iii) may be performed according to any one of the methods described herein above. This may require specifically chosen or adapted recombinant cells, which are also described herein-above.

Confirmation of Identified Modulators:

A modulator identified by a method described herein-above may easily be confirmed by simple sensory experiments using a panel of test persons to smell samples as detailed below. The samples have been exposed to a peptidase and a β-lyase and contain as a substrate a compound of formula FI below and any formed enzymatic reaction products.

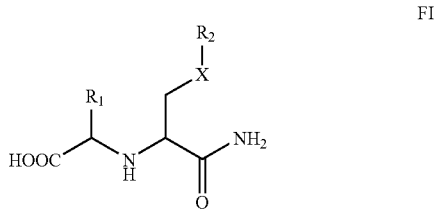

FI wherein X is selected from S and wherein R1 is residue selected from the group consisting of H and methyl and wherein R2 is a residue selected from the group consisting of a C1 to C10 alkyl, C1 to 010 alkanol, a phenyl, and a benzyl.

The samples are smelled by the panel in comparison to a negative control without modulator to confirm a modulator that modulates, for example inhibits, malodour formation.

Large Scale Screening Assays:

The assays described herein-above are well suited for screening libraries for agents that modulate peptidase activity.

The assays may be designed to screen large chemical libraries by automating the assay steps and providing compounds from any convenient source to the assays, which are typically run in parallel (for example in microtiter formats on microtiter plates in robotic assays).

Assays may be run in high throughput screening methods that involve providing a combinatorial chemical or peptide library containing a large number of potential modulators. Such libraries are then screened in one or more assays described herein-above to identify those library agents (particular chemical species or subclasses) that display the activity described herein-above. The modulators thus identified can be directly used or may serve as leads to identify further modulators by making and testing derivatives.

Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.).

Binding Assays:

Alternatively to the functional methods described herein-above that measure a change in cleavage/reaction rate by measuring increase or decrease of educts and direct or indirect products (for example, without limitation, substrate/precursor I, precursor II, malodourant), substrate binding may be determined by binding assays that measure the binding of a substrate to the peptidase, which are well known in the art. Binding of a modulator to a peptidase polypeptide can be determined, for example, without limitation, by measuring changes in spectroscopic characteristics (for example fluorescence, absorbance, or refractive index), hydrodynamic methods (employing for example shape), chromatography, measuring solubility properties of a peptidase polypeptide.

Libraries of Test Agents:

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

A rare chemical library is available from Aldrich (Milwaukee, Wis.).

Libraries of natural compounds in the form of bacterial, fungal, plant and animal extracts are commercially available for example from Pan Laboratories (Bothell, Wash.) or Myco-Search (NC), or are readily produceable by methods well known in the art. Additionally, natural and synthetically produced libraries and compounds are readily modified through conventional chemical, physical, and biochemical means.

Other libraries include protein/expression libraries, cDNA libraries from natural sources, including, for example, foods, plants, animals, bacteria, libraries expressing randomly or systematically mutated variants of one or more polypeptides, genomic libraries in viral vectors that are used to express the mRNA content of one cell or tissue.

In a high throughput assay, it is possible to screen up to several thousand different modulators or substrates in a single day. In particular, each well of a microtiter plate can be used to run a separate assay against a selected potential modulator/substrate, or, if concentration or incubation time effects are to be observed, every 5-10 wells can test a single modulator. Thus, a single standard microtiter plate can assay about 100 modulators. If 1536 well plates are used, then a single plate can easily assay from about 100 to about 1500 different compounds. It is possible to assay several different plates per day; assay screens for up to about 6,000-20,000 different compounds is possible.

Types of Test Agents that May be Tested for their Peptidase Modulating Effect in the Assay Methods:

The test agents may be any agent including small chemical compounds, chemical polymers, biological polymers, peptides, proteins, sugars, carbohydrates, nucleic acids and lipids. An agent can be a synthetic compound, a mixture of compounds, a natural product or natural sample, for example plant extract, culture supernatant, or tissue sample.

Personal Care Products:

The identified enzyme inhibitors/malodour counteractants may be added to various products to prevent body malodour. For example, personal care products include, without limitation, deodorant, antiperspirant, lotion, cream, salve, powder, body lotion, unguent, soap, shampoo, fine fragrance, eau de Cologne, eau de toilet. Personal care products may be perfumed or may be perfume-free. Such products usually contain a number of excipients that are well known in the art. The malodourcounteractant effect of personal care products can be further improved by leaving out any ingredients indentified as enhancers of peptidase.

The identified modulator/inhibitor may be added to an aqueous solution, emulsion, alcoholic solution, silicon solution, oil or wax.

Sequences of Nucleic Acids and Proteins:

The sequences employed in the constructs and methods described-herein can be found in the sequence listing hereinbelow.

SEQ ID NO: 1: Nucleotide sequence of peptidase from *Corynebacterium* sp. Ax20

SEQ ID NO: 2: Aminoacid sequence of peptidase from *Corynebacterium* sp. Ax20

SEQ ID NO: 3: Nucleotide sequence of peptidase from *Corynebacterium jeikeium* K411

SEQ ID NO: 4: Aminoacid sequence of peptidase from *Corynebacterium jeikeium* K411

SEQ ID NO:5: Nucleotide sequence of β-lyase from *Corynebacterium* sp. Ax20

SEQ ID NO:6: Aminoacid sequence of β-lyase from *Corynebacterium* sp. Ax20

There now follows a series of examples that serve to illustrate the above-described subject matter. The following examples are merely illustrative and should not be construed as limiting the subject matter described herein including polypeptides, nucleic acids/nucleotides, expression vectors, host cells, methods, kit and personal care products in any manner.

EXAMPLES

All examples use the DNA sequences derived from *Corynebacteria*, in particular *Corynebacterium* sp. Ax20 ("Ax20"), DSM 14267, which has been submitted on the 26, April 2001 to the International Depository Authority DSMZ-German Collection of Microorganisms and Cell Cultures, D-38124 Braunschweig (Accession Number DSM 14267), and *Corynebacterium jeikeium* K411 ("K411") (Tauch et al. 2005, J. Bacteriol. 187(13): 4671-82).

In the examples, the cys-gly-conjugate refers to the following dipeptide compound:

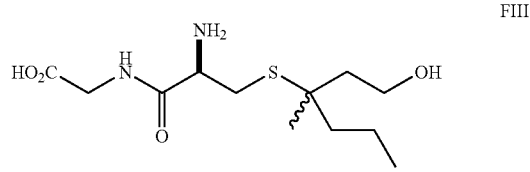 [SMILES: CCCC(C)(CCO)SC[C@H](N)C(=O)NCC(=O)O]

FIII

The cys-conjugate in the examples refers to the following compound:

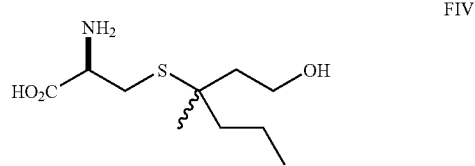

FIV

"β-lyase" in the examples refers to the β-lyase enzyme described in Natsch et al. 2004, Chemistry & Biodiversity, 1, 1058. The full open reading frame of the β-lyase gene (metC gene, 1134 bp) is available from Genebank under the accession number AY646680 (gi|51556860|gb|AY646680.1| [51556860]). It is also included in the sequence listing (SEQ ID NO:5, nucleotide sequence, and SEQ ID NO:6, protein sequence).

"AMRE" or "AMRE enzyme" is short for "axilliary malodour releasing enzyme" and designates the malodourous acid releasing enzyme Nα-acyl-glutamine-aminoacylase described by Natsch in EP1258531. The AMRE aminoacid sequence is SEQ ID NO: 1 in EP 1258531, the open reading frame of the AMRE gene is SEQ ID NO:5 in EP1258531. It's heterologous expression is described in example 6 of EP1258531

Example 1

Isolation of Peptidase (SEQ ID NO:2)

A cellular extract was formed as follows: an overnight culture of Ax20 was harvested by centrifugation and resuspended in a small volume of Buffer A (50 mM NaCl; 50 mM NaH2PO4/K2HPO4; pH 7), amended with a 10-fold volume of glass beads (425-600 µm, Sigma, St-Louis, USA) and mechanically disrupted by vortexing them at maximal speed for 30 min. The lysates were centrifugated and the supernatants were saved. The resulting *Corynebacterium* sp. Ax20 cellular extract was then subsequently fractionated over the following columns: 1. Phenyl-sepharose (hydrophobic interaction chromatography), 2. Mono-Q (strong anion exchange), 3. Mono-P (weak anion exchange) and 4. Superdex 200 (gel filtration).

Samples of each fraction were incubated both with the β-lyase and with the cys-gly-conjugate at the same time, and the release of 3-sulfanyl-3-methyl-hexanol was determined by a fluorescence test specific for free SH groups: To this end the enzyme reaction was stopped by adding 0.5 volumes of NaCO3-buffer (0.1 M, pH 8.8) containing 0.5 mM monobromobimane, thus derivatising the free thiol-group. Fluorescence was then measured on a Flex-station (Molecular devices, Sunnyvale, Calif., USA) with an excitation wavelength of 385 nm and an emission wavelength of 480 nm.

A single peak of activity (3-sulfanyl-3-methyl-hexanol release) was found in each purification step, indicating that only one enzyme is involved in the release reaction.

After these four purification steps, the preparation was separated on a SDS-Page-gel. The gel band unique to the active fractions was excised and the peptidase thereby obtained.

Example 2

Cloning of the Gene (SEQ ID NO:1) and Isolation of the Nucleic Acid Sequence Coding for the Peptidase (SEQ ID NO:2)

The peptidase obtained in example 1 was submitted to a tryptic digest and peptide sequence analysis. Based on these isolated peptides sequences, primers were designed to amplify a partial sequence of the gene by polymerase chain reaction using genomic DNA of *Corynebacterium* sp. Ax20 as a template.

The complete gene sequence was then isolated by chromosomal walking with a chromosomal library of *Corynebacterium* sp. Ax20.

Thereby the complete open reading frame of the peptidase sequence was obtained as shown in SEQ ID NO:1.

Example 3

Heterologous Expression, Production and Purification of the Ax20 Peptidase

The open reading frame (ORF) of the peptidase (SEQ ID NO:1) was amplified from chromosomal DNA of *Corynebacterium* sp. Ax 20 by PCR using specific primers. The ORF was ligated to a sequence coding for a 6× Histidine-Tag and cloned into an expression vector (pET-3a, Studier and Moffatt, 1986). The resulting plasmids were transformed into an *E. coli* strain (BL21(DE3)).

Alternatively, the ORF without the 6× Histidine-Tag was cloned into the same vector.

The recombinant *E. coli* strains with or without 6× Histidine-Tag were grown in NZCYM medium (Casein hydrolysate 10.0 g; NaCl 5.0 g; Casamino acids (Difco) 1.0 g; Yeast extract 5.0 g; MgSO4×7H2O 2.0 g; Maltose 2.0 g; Distilled water 1000.0 ml), induced with IPTG (Isopropyl-β-D-thiogalactopyranosid) and after 4 h the cells were lysed by three passages through a french press in a phosphate buffer (100 mM, pH7). The cell lysate was cleared by centrifugation at 10'000 g for 15 minutes.

To purify the enzyme, the clear cell lysate was loaded onto a Ni-NTA affinity column (Qiagen, Hilden, Germany). The column was washed with a buffer containing 20 mM imidazole and finally eluted with a buffer with an increasing concentration of 100-250 mM imidazole. The resulting eluate contained the recombinant enzyme in >95% purity as shown by SDS page.

Example 4

Heterologous Expression and Production of the K411 Peptidase (SEQ ID NO:4)

The SEQ ID NO: 4 peptidase from *Corynebacterium* K411 was expressed, produced and purified as described above for SEQ ID: NO:2.

Example 5

Activity of Ax20 and K411 Peptidases 50 ml of recombinant *E. coli* culture formed as described in example 3 and 4 was harvested, resuspended in a final volume of 3 ml of phosphate buffer and then disrupted with ultrasonication. The soluble extract was cleared by centrifugation. Different dilutions of the resulting extract were incubated with the cys-gly-conjugate (1 mM) and in presence as well as in absence of an excess of the β-lyase. As a negative control, clear cell lysate from *E. coli* transformed with an empty vector, and cell lysates with the cys-gly-conjugate but no β-lyase were used.

The table shows the release of the malodourant (3-sulfanyl-3-methyl-hexanol) in mM as determined with the fluorescence test described in example 1.

As shown in the table below, see columns 2 to 4, the malodourant (3-sulfanyl-3-methyl-hexanol) was only released from the cys-gly-conjugate by the recombinant *E. coli* strain transformed with the plasmid containing SEQ ID NO:1 or SEQ ID NO:3 (expressing SEQ ID NO: 2/Ax20 or SEQ ID NO: 4/K411 peptidase) and only in presence of the 3-lyase. K411 peptidase cleaves the cys-gly-conjugate (see column 5) with a lower efficacy than Ax20 peptidase.

| | release of 3-sulfanyl-3-methyl-hexanol from the Cys-Gly-conjugate [mM] | | | | | |
|---|---|---|---|---|---|---|
| Dilution of clear cell lysate | Negative control (empty vector) + β-lyase | Ax20 peptidase w/o β-lyase | Ax20 peptidase + β-lyase | Ax20 peptidase with histidine tag + β-lyase | K411 peptidase w/o β-lyase | K411 peptidase + β-lyase |
| 10 fold | 0.10 | 0.10 | 1.00 | 0.94 | 0.10 | 0.55 |
| 100 fold | 0.01 | <0.01 | 0.92 | 0.88 | <0.01 | 0.19 |
| 1000 fold | 0.00 | <0.01 | 0.46 | 0.36 | <0.01 | 0.03 |

This shows that the isolated nucleotide sequence of SEQ ID NO:1 and SEQ ID NO:3 codes for a peptidase enzyme with the relevant enzymatic activity.

As shown, the histidine tag does not have any significant effect on peptidase activity.

Example 6

Substrate Specificity of Ax20 Peptidase

The recombinant Ax20 peptidase formed as described in example 3 (affinity column purified tagged enzyme) was incubated with different compounds, in particular potential candidate dipeptide substrates, to characterize the substrate specificity and to identify substrates useful for screening assays (for example to screen for modulators including inhibitors).

The table below lists the tested compounds (mostly dipeptides indicated by their short names, e.g. ala-gly for an alanine-glycine dipeptide) and indicates whether they are cleaved by the peptidase. Z indicates a benzyloxy-carbonyl protecting group at the N-terminus of the peptide.

Cleavage was determined by thin layer chromatography.

Amounts are qualitative with (+++) indicating >80% cleavage of a 1 mM solution by 0.1 μg/ml peptidase during an incubation for 1 h; (++) indicates complete cleavage of a 1 mM solution by 1 μg/ml peptidase during an incubation for 1 h and (+) indicates partial cleavage (20-80%) of a 1 mM solution by 1 μg/ml peptidase during an incubation for 1 h and (−) indicating the absence of any cleavage.

| Compounds/Potential substrates | Cleavage |
|---|---|
| Cys-gly-conjugate | +++ |
| H-Cys(Bzl)-Gly-OH (=S-benzyl-Cys-Gly) | +++ |
| Ala-Gly | ++ |
| Ala-Ala | ++ |
| Gly-Gly | + |
| Pro-Gly | + |
| Z-Gly-Gly | − |
| Z-Ala | − |
| Z-Gly | − |

Example 7

Method to Identify Peptidase Modulators/Inhibitors

Cleavage of the peptide substrate Pro-Gly by addition of the recombinant Ax20 peptidase (SEQ ID NO: 2) released a unique free $NH_2$ group which can be derivatized by fluorescamine (Fluram™, Fluka, Buchs, Switzerland).

Test compounds (for example, potential enzyme inhibitors) are dissolved in dimethylsulfoxid (DMSO), for example in individual wells of a microtiter plate.

Ax20 peptidase dissolved in a phosphate buffer is added to the individual wells of the microtiter plate (1 μg/ml peptidase), and incubated for 5 min to allow equilibration and binding of the inhibitors, if any, to the peptidase.

The substrate Pro-Gly dissolved in phosphate buffer is added to the test compound/peptidase mix in each well to give a final concentration of 1 mM.

Alternatively, another substrate compound may be used. Useful substrates include Ala-Ala, Ala-Gly, the Cys-gly-conjugate and S-benzyl-Cys-Gly. If these compounds are used, detection of the cleavage is performed by determining the formed free glycine (by Thin-layer chromatography (TLC) or by high performance liquid chromatography (HPLC)), instead of by fluorometry.

After an incubation time of 60 min at 37° C., the free $NH_2$ group of the glycine released from Pro-Gly is derivatised by adding Fluram dissolved in acetonitrile to a final Fluram concentration of 1 mM and a final acetonitrile concentration of 25% v/v, and after 5 min incubation, the fluorescence is determined on a Flex-station (Molecular devices, Sunnyvale, Calif., USA) with an excitation wavelength of 381 nm and an emission wavelength of 470 nm. Controls are run in parallel and subjected to the same procedure. A positive control contains DMSO without inhibitor, a negative control contains no substrate.

% inhibition is calculated based on a comparison with the positive control (0% inhibition/100% activity). Examples of active inhibitors thus identified are shown in the table below.

| Test compound | c [microM] | Inhibition of release of free $NH_2$ groups from Pro-Gly [% inhibition] |
|---|---|---|
| Ethylenediaminetetraacetic acid | 62.5 | 101.4 |
| Ethylenediaminetetraacetic acid | 31.25 | 102.6 |
| Ethylenediaminetetraacetic acid | 15.625 | 101.0 |
| o-Phenantrolin | 62.5 | 100.0 |
| o-Phenantrolin | 31.25 | 95.5 |
| o-Phenantrolin | 15.625 | 83.9 |
| pyridine-2,6-dicarboxylic acid | 62.5 | 100.9 |
| pyridine-2,6-dicarboxylic acid | 31.25 | 92.4 |
| pyridine-2,6-dicarboxylic acid | 15.625 | 72.4 |
| ethylendiamine-N,N'-diacetic acid | 62.5 | 93.9 |
| ethylendiamine-N,N'-diacetic acid | 31.25 | 81.0 |
| ethylendiamine-N,N'-diacetic acid | 15.625 | 65.7 |
| 2,2'-Ethylendithio-diacetic acid | 62.5 | −5.3 |
| 2,2'-Ethylendithio-diacetic acid | 31.25 | −2.6 |
| 2,2'-Ethylendithio-diacetic acid | 15.625 | 0.1 |

The results in the table show that the compound Pro-Gly is a useful substrate for high-throughput screening. The only NH2 group present is the one in Gly released through cleavage by the peptidase, allowing for a superior signal to noise ratio.

An inhibitor is usually identified by an inhibition of at least 50% inhibition, for example at a concentration of 1 mM, 100 microM, 10 microM, 1 microM, or below.

Example 7b

Method to Identify Peptidase Modulators/Inhibitors Using Various Peptidase Enzymes Example 7 may be performed as described with the exception of replacing the peptidase enzyme and using one or more of SEQ ID NO:4 (K411 peptidase), or a homolog to SEQ ID NO: 4 or SEQ ID NO: 2 (Ax20 peptidase).

Example 7c

Method to Identify Peptidase Modulators/Inhibitors with Broad Inhibitory Spectrum Example 7 may be performed as described with the exception of using two or more peptidase enzymes selected from SEQ ID NO:2, SEQ ID NO:4, or a homolog to SEQ ID NO: 4 or SEQ ID NO: 2, subsequently or in parallel. When performed in parallel, the enzymatic reactions may be performed in the same well using a compatible buffer.

This has the advantage to identify compounds that act on both peptidases and identify inhibitory compounds with a broad inhibitory activity against various bacterial strains.

Example 8

Method to Identify Peptidase Modulators/Inhibitors that are Active Against Peptidase and/or β-lyase The example was performed as an alternative to the screening assay as described in example 7, with the following modifications.

As substrates, the cys-gly-conjugate or the compounds of the substrate structure as described herein above are used.

These include (S-benzyl)-cys-gly, (S-benzyl)-cys-ala, or any S-substituted cys-gly or cys-Ala conjugate, for example, S-ethyl-, S-propyl-, S-butyl-, S-pentyl-, S-hexyl-, S-phenyl-cys-gly or -cys-ala.

Alternatively, substituted ser-ala or ser-gly derivatives are used which are substituted at the OH group of serine. The same wide variety of substituents at serine are possible as with cysteine.

For the results shown below (S-benzyl)-cys-gly was used.

The peptidase (SEQ ID NO:2) in a concentration of 0.1 μg/ml was used in combination with β-lyase in a concentration of 5 μg/ml; both enzymes were dissolved in the same phosphate buffer at the same time.

Simultaneously screening inhibitors of both β-lyase and peptidase has the advantage of a more effective screen (i.e. both inhibitors of either the peptidase or the β-lyase or both are identified at the same time). Subsequently each screening "hit" (modulation/inhibition of release of malodourant) was further analyzed to determine peptidase activity and/or β-lyase activity separately.

Instead of derivatising the free $NH_2$ group of the conjugate by adding Fluram, the free SH group released from the conjugate by the subsequent action of both enzymes was derivatised by adding monobromobimane (Fluka, Buchs, Switzerland) dissolved in a $NaCO_3$ buffer (100 mM, pH 8.8) to give a final concentration of 0.5 mM to 1 mM. After 5 to 15 min incubation the fluorescence was measured on a Flex-station (Molecular devices, Sunnyvale, Calif., USA) with an excitation wavelength of 385 nm and an emission wavelength of 480 nm.

Alternatively other thiol-derivatizing agents were used including N-(9-acridinyl)maleimide and fluorescent detection at 359/440 nm.

Active peptidase inhibitors thus identified are shown in the table below.

| Test compound | c [microM] | Inhibition of release of free SH groups from S-benzyl-cys-gly in presence of peptidase and β-lyase [% inhibition] |
|---|---|---|
| Ethylenediaminetetraacetic acid | 62.5 | 99.0 |
| Ethylenediaminetetraacetic acid | 31.25 | 96.5 |
| Ethylenediaminetetraacetic acid | 15.625 | 99.3 |
| o-Phenantrolin | 62.5 | 93.1 |
| o-Phenantrolin | 31.25 | 79.9 |
| o-Phenantrolin | 15.625 | 54.2 |
| pyridine-2,6-dicarboxylic acid | 62.5 | 95.9 |
| pyridine-2,6-dicarboxylic acid | 31.25 | 83.4 |
| pyridine-2,6-dicarboxylic acid | 15.625 | 49.6 |
| ethylendiamine-N,N'-diacetic acid | 62.5 | 90.4 |
| ethylendiamine-N,N'-diacetic acid | 31.25 | 73.1 |
| ethylendiamine-N,N'-diacetic acid | 15.625 | 50.2 |
| 2,2'-Ethylendithio-diacetic acid | 62.5 | −8.7 |
| 2,2'-Ethylendithio-diacetic acid | 31.25 | −9.1 |
| 2,2'-Ethylendithio-diacetic acid | 15.625 | −10.1 |

Example 9

Method to Identify Broad-Band Modulators/Inhibitors Active Against One or More Peptidase (SEQ ID NO: 2 and/or NO: 4) and AMRE In an additional step to example 7 or 8, the identified peptidase inhibitors were tested for their modulating effect against the AMRE enzyme (Na-acyl-glutamine-aminoacylase described by Natsch in EP1258531), thereby identifying dual inhibitors of both metallopeptidase enzymes involved in malodour release.

Alternatively, the steps can be performed in parallel in presence of the enzymes at the same time.

AMRE is formed as described in example 6 of EP1258531.

The results are listed in the table below.

| Test compound | c [microM] | Inhibition of release of free NH2 groups from N-Lauroyl-glutamine (catalyzed by AMRE) [% inhibition] |
|---|---|---|
| Ethylenediaminetetraacetic acid | 62.5 | 61.6 |
| Ethylenediaminetetraacetic acid | 31.25 | 59.8 |
| Ethylenediaminetetraacetic acid | 15.625 | 62.4 |
| o-Phenantrolin | 62.5 | 96.1 |
| o-Phenantrolin | 31.25 | 81.8 |
| o-Phenantrolin | 15.625 | 42.4 |
| pyridine-2,6-dicarboxylic acid | 62.5 | 72.2 |
| pyridine-2,6-dicarboxylic acid | 31.25 | 52.0 |
| pyridine-2,6-dicarboxylic acid | 15.625 | 28.8 |
| ethylendiamine-N,N'-diacetic acid | 62.5 | 42.7 |
| ethylendiamine-N,N'-diacetic acid | 31.25 | 7.2 |
| ethylendiamine-N,N'-diacetic acid | 15.625 | 7.4 |
| 2,2'-Ethylendithio-diacetic acid | 62.5 | 19.6 |
| 2,2'-Ethylendithio-diacetic acid | 31.25 | 12.7 |
| 2,2'-Ethylendithio-diacetic acid | 15.625 | 22.4 |

Thus the results demonstrate that active inhibitors, in this case metal chelators, active against more than one malodour forming enzyme, can be identified with a combination of the assays as described, thereby allowing for an effective assay to identify broad-band modulators/inhibitors.

Example 10

Differences in Cleavage of the cys-gly-Conjugate when Cleaved with Ax20 Cell Lysate or β-lyase The test compounds (Cys-conjugate (1 mM) or Cys-Gly-conjugate (1 mM)) were incubated with β-lyase.

The test compounds (cys-conjugate (1 mM) or cys-gly-conjugate (1 mM)) were incubated also with the wild-type strain *Corynebacterium* sp. Ax20 extract naturally containing the peptidase of SEQ ID NO:2. *Corynebacterium* sp. Ax20 cellular extract was prepared as described in example 1. The resulting extract was diluted to the same volume as the original culture has had when adjusted to an optical density of OD 4. The substrate was incubated with the extract for 24 h.

Cleavage was measured by gas chromatography to determine the release of 3-sulfanyl-3-methyl-hexanol in mM. The results are shown in the table below.

|  | release of 3-sulfanyl-3-methyl-hexanol from cys-conjugate [mM] | release of 3-sulfanyl-3-methyl-hexanol from cys-gly-conjugate [mM] |
| --- | --- | --- |
| β-lyase | 0.59 | <0.03 |
| C. sp. Ax20 extract | 0.31 | 0.21 |

The results show that only the cys conjugate but not the cys-gly-conjugate was cleaved by the recombinant β-Lyase, indicating that the β-Lyase cannot cleave the main substrate in the axilla secretion (see row 2 of the table above).

However, the extract from *C.* sp. Ax 20 isolated from the axilla of a human test subject does release 3-sulfanyl-3-methyl-hexanol from both conjugates (see row 3 of the table above).

Example 11

Separate *C.* sp. Ax20 Extract Fractions are not able to Release Malodourant

Cellular extracts obtained from *C.* sp. Ax20 as described in example 1 were fractionated using a Mono-Q anion exchange column. The resulting fractions were separately incubated with the cys-gly-conjugate and the release of 3-sulfanyl-3-methyl-hexanol (malodourant) was measured as described in example 1.

The results showed that no single fraction of *C.* sp. Ax20 extract was able to release 3-sulfanyl-3-methyl-hexanol from the cys-gly-conjugate. This demonstrates that there is no single enzyme present in *C.* sp. extracts that can release the malodourant from the cys-gly-conjugate.

Example 12

*C.* sp. Extract Fraction Releases Malodourant when Combined with β-lyase

Fractions of *C.* sp. Ax20 cellular extracts were formed as described in example 11.

Each fraction was incubated with β-lyase and with the cys-gly-conjugate. The release of 3-sulfanyl-3-methyl-hexanol (malodourant) was measured as described in example 1 above.

The results showed that a single fraction released 3-sulfanyl-3-methyl-hexanol from the cys-gly-conjugate in presence of the β-lyase. The other fractions or β-lyase on its own were not able to release the malodourant.

Together with the results of example 11 this demonstrates that two enzymes are mediating the cleavage of the cys-gly-conjugate: first the peptidase cleaving the dipeptide between the gly and the cys residue, and then a β-lyase subsequently releasing the malodourant from the cys-conjugate formed by the peptidase.

Example 13

Malodour Release by *Corynebacteria* Extract is Inhibited by Peptidase Inhibitors Extracts from *C.* sp. Ax20 and *C. jeikeium* K411 were formed as described in example 1.

O-phenantrolin (0.5 mM), a metallopeptidase inhibitor, or Complete™ (EDTA free), a protease inhibitor mix (Roche biochemicals, Switzerland; use concentration as indicated by the manufacturer) that contains broad specificity serine and aspartate-peptidases inhibitors but no metallopeptidase inhibitors were added to batches of the extracts and incubated for 10 min.

The cys-conjugate or the cys-gly-conjugate (1 mM), both precursors for the malodourant 3-sulfanyl-3-methyl-hexanol, were then added to the *C.* sp. Ax20 or *C. jeikeium* K411 extracts containing the different inhibitors.

The release of the malodourant 3-sulfanyl-3-methyl-hexanol, which indicates enzyme activity in the *Corynebacteria* cell lysates, was measured as described in examples 12 and 13.

The results (in % inhibition of 3-sulfanyl-3-methyl-hexanol release compared to reactions without added inhibitors) are indicated in the table below.

|  | *C.* sp. Ax20 | | *C. jeikeium* K411 | |
| --- | --- | --- | --- | --- |
|  | Cys-conj. | Cys-Gly-conj. | Cys-conj. | Cys-Gly-conj. |
| o-phenantrolin | 0 | 100 | 13 | 93 |
| Complete ™ | 1 | 0 | 14 | 37 |

As shown in example 10, incubation with *C.* sp. Ax20 extract induced a significant malodourant release from both conjugates, and *C. jeikeium* K411 extract also cleaved both substrates, though at a lower rate.

The addition of the metallopeptidase inhibitor o-phenanthrolin does not inhibit Cys-conjugate cleavage (0% inhibition) but inhibits cys-gly-conjugate cleavage (100% inhibition) when extract from *C.* sp. is used. Similarly, for *C. jeikeium* extract, there is no significant inhibition for the cys-conjugate but high inhibition of the cys-gly-conjugate (93%).

This shows that the cleavage of the cys-gly-conjugate (but not the cys-conjugate) is mediated by an enzyme susceptible to inhibition by metallopeptidase inhibitor o-phenanthrolin.

This also indicates that the β-lyase reaction (Cleavage of the Cys-conjugate) is not blocked by o-phenanthrolin, but only the cleavage of the cys-gly bond is inhibited, and shows that a metallopeptidase in extracts from *Corynebacteria* exclusively catalyses this reaction.

The mixture of protease inhibitors (Complete™) with broad specificity for different serine and aspartate-peptidases did not significantly block cleavage of either conjugate, showing that no serine/aspartate-peptidase is involved in the release of the malodourant.

While the peptidases, nucleotides, expression vectors, host cells, methods and kit have been described above in connection with certain illustrative embodiments, it is to be understood that other similar embodiments may be used or modifications and additions may be made to the described embodiments for performing the same function(s). Further, all embodiments disclosed are not necessarily in the alternative, as various embodiments may be combined to provide the desired characteristics. Variations can be made by one having ordinary skill in the art without departing from the spirit and scope of the disclosure. Therefore, the nucleotides, polypeptides/peptidases, expression vectors, host cells, methods and kit should not be limited to any single embodiment, but rather construed in breadth and scope in accordance with the recitation of the attached claims.

The invention claimed is:

1. A method of inhibiting a peptidase in its ability to cleave its substrate wherein the peptidase is contacted with a peptidase inhibitor wherein the peptidase inhibitor is a non-physiological substrate of formula FI

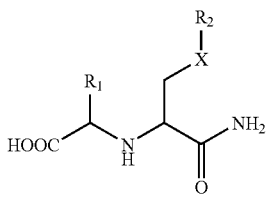

wherein X is selected from the group consisting of S and O, and wherein $R_1$ is residue selected from H and methyl, and wherein $R_2$ is a residue selected from the group consisting of a straight or branched $C_1$ to $C_{10}$ alkyl, a straight or branched $C_1$ to $C_{10}$ alkanol, a phenyl, and a benzyl, and wherein the peptidase has the catalytic activity to release glycine from the substrate compound of formula FIII

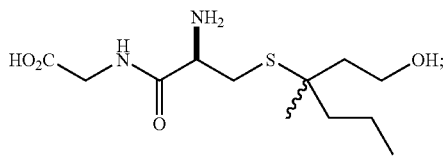

wherein the peptidase is homologous to a polypeptide sequence selected from the group consisting of SEQ ID NO: 2 and SEQ ID NO: 4 with a sequence identity of at least 40%;

wherein the peptidase comprises the following conserved partial sequences:

ERDGRWYGRGXADCKG between amino acid 113 and 128 in SEQ ID NO: 2, and between amino acid 119 and 134 in SEQ ID NO: 4;

EGSEEXG between amino acid 155 and 161 in SEQ ID NO: 2 and between amino acid 167 and 173 in SEQ ID NO: 4;

HSGXXGGXAPDA between amino acid 219 and 230 in SEQ ID NO: 2 and between amino acid 230 to 241 in SEQ ID NO: 4;

GGSIPL between amino acid 397 to 402 in SEQ ID NO: 2 and between amino acid 406 to 411 in SEQ ID NO: 4;

and wherein the amino acids are numbered starting from the N-terminus of a substantially homologous peptidase in its naturally occurring form, and the letters refer to the single character amino acid code and X is any one of the 20 common amino acids.

2. A method for preventing or reducing the formation of body malodour wherein a peptidase inhibitor is applied to a body surface wherein the peptidase inhibitor is a non-physiological substrate of formula FI

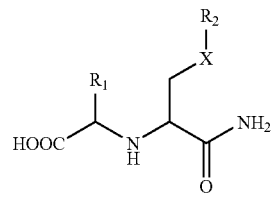

wherein X is selected from the group consisting of S and O, and wherein $R_1$ is residue selected from H and methyl, and wherein $R_2$ is a residue selected from the group consisting of a straight or branched $C_1$ to $C_{10}$ alkyl, a straight or branched $C_1$ to $C_{10}$ alkanol, a phenyl, and a benzyl, wherein the peptidase has the catalytic activity to release glycine from the substrate compound of formula FIII

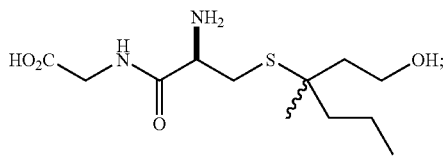

wherein the peptidase is homologous to a polypeptide sequence selected from the group consisting of SEQ ID NO: 2 and SEQ ID NO: 4 with a sequence identity of at least 40%;

wherein the peptidase comprises the following conserved partial sequences:

ERDGRWYGRGXADCKG between amino acid 113 and 128 in SEQ ID NO: 2, and between amino acid 119 and 134 in SEQ ID NO: 4;

EGSEEXG between amino acid 155 and 161 in SEQ ID NO: 2 and between amino acid 167 and 173 in SEQ ID NO: 4;

HSGXXGGXAPDA between amino acid 219 and 230 in SEQ ID NO: 2 and between amino acid 230 to 241 in SEQ ID NO: 4;

GGSIPL between amino acid 397 to 402 in SEQ ID NO: 2 and between amino acid 406 to 411 in SEQ ID NO: 4;

and wherein the amino acids are numbered starting from the N-terminus of a substantially homologous peptidase in its naturally occurring form, and the letters refer to the single character amino acid code and X is any one of the 20 common amino acids.

3. The method according to claim 1 wherein the non-physiological peptidase inhibitor is applied in a form of a dermatologically acceptable composition comprising at least one excipient.

* * * * *